(12) United States Patent
Siewerdsen et al.

(10) Patent No.: US 11,596,367 B2
(45) Date of Patent: Mar. 7, 2023

(54) ELECTROMAGNETIC TRACKING SYSTEM AND METHODS OF USING SAME

(71) Applicant: THE JOHNS HOPKINS UNIVERSITY, Baltimore, MD (US)

(72) Inventors: Jeffrey H. Siewerdsen, Baltimore, MD (US); Jongheun Yoo, Baltimore, MD (US)

(*) Notice: Subject to any disclaimer, the term of this patent is extended or adjusted under 35 U.S.C. 154(b) by 326 days.

(21) Appl. No.: 16/742,034

(22) Filed: Jan. 14, 2020

(65) Prior Publication Data
US 2020/0229777 A1 Jul. 23, 2020

Related U.S. Application Data

(63) Continuation of application No. 14/117,100, filed as application No. PCT/US2012/037530 on May 12, 2012, now Pat. No. 10,575,797.

(60) Provisional application No. 61/485,582, filed on May 12, 2011.

(51) Int. Cl.
| | |
|---|---|
| A61B 6/00 | (2006.01) |
| A61B 6/04 | (2006.01) |
| G01R 33/028 | (2006.01) |
| A61B 6/03 | (2006.01) |
| A61B 34/20 | (2016.01) |
| A61B 5/06 | (2006.01) |
| A61G 13/04 | (2006.01) |

(52) U.S. Cl.
CPC ............ *A61B 6/0407* (2013.01); *A61B 5/061* (2013.01); *A61B 6/032* (2013.01); *A61B 6/4085* (2013.01); *A61B 6/4441* (2013.01); *A61B 6/547* (2013.01); *A61B 6/582* (2013.01); *A61B 6/583* (2013.01); *A61B 34/20* (2016.02); *A61G 13/04* (2013.01); *G01R 33/028* (2013.01); *A61B 6/4405* (2013.01); *A61B 6/4423* (2013.01); *A61B 6/508* (2013.01); *A61B 2034/2051* (2016.02); *A61G 2200/322* (2013.01)

(58) Field of Classification Search
None
See application file for complete search history.

(56) References Cited

U.S. PATENT DOCUMENTS

| | | | |
|---|---|---|---|
| 6,484,049 B1 | 11/2002 | Seeley et al. | |
| 6,636,757 B1 | 10/2003 | Jascob et al. | |
| 7,103,931 B2 | 9/2006 | Somasundaram et al. | |
| 7,609,062 B2 | 10/2009 | Roland | |
| 2002/0085681 A1* | 7/2002 | Jensen | A61B 6/463 378/197 |

(Continued)

FOREIGN PATENT DOCUMENTS

| | | |
|---|---|---|
| EP | 1421900 A1 | 5/2004 |
| WO | 2012155050 A2 | 11/2012 |

OTHER PUBLICATIONS

Biosense Webster Carlo XP Brochure, 2004.
Bo, et al., (2011) "Accuracy of electromagnetic tracking with a prototype field generator in an interventional or setting" Med. Phys. 39(1) 399-406.

(Continued)

*Primary Examiner* — Joel F Brutus

(57) ABSTRACT

An electromagnetic tracking system including a patient support element and an electromagnetic field generator. The patient support element is superposed relative to the electromagnetic field generator, and the electromagnetic field generator is selectively moveable relative to the patient support element.

26 Claims, 13 Drawing Sheets

(56) References Cited

U.S. PATENT DOCUMENTS

| | | | | |
|---|---|---|---|---|
| 2002/0100486 A1* | 8/2002 | Creighton, IV | ....... | A61B 34/73 |
| | | | | 128/899 |
| 2005/0046530 A1* | 3/2005 | Vittorio | ............ | G01R 33/34053 |
| | | | | 335/216 |
| 2006/0025668 A1* | 2/2006 | Peterson | ................ | A61B 5/062 |
| | | | | 600/407 |
| 2007/0003010 A1* | 1/2007 | Guertin | ................ | A61B 6/4441 |
| | | | | 378/63 |
| 2007/0007897 A1* | 1/2007 | Billings | ................ | H01J 61/302 |
| | | | | 313/493 |
| 2009/0281566 A1 | 11/2009 | Edwards et al. | | |
| 2009/0306495 A1 | 12/2009 | Scarth et al. | | |
| 2011/0224537 A1 | 9/2011 | Brunner | | |

OTHER PUBLICATIONS

Yoo, J., et al., (2013) "An electromagnetic 'tracker-in-table' configuration for x-ray fluoroscopy and cone-beam ct-guided surgery" Int. J. CARS, 8. pp. 1-13.

Yoo, J., et al., (2011) An x-ray compatible electromagnetic field generator in cone-beam CT-guided surgery: Characterization and implementation; Presentation.

Yoo, J., et al., (2011) "Characterization and implementation of an x-ray compatible electromagnetic field generator in cone-beam CT-guided surgery" CARS pp. 1-3.

IPRP and Written Opinion dated Jan. 3, 2013 for PCT/US2012/037530.

Aurora Brochure; NDI Electromagnetic Tracking Technology (2014) Aurora Features and Benefits.

\* cited by examiner

MOBILE C-ARM IN
POSTERIOR ANTERIOR POSE

MOBILE C-ARM IN
LATERIOR POSE

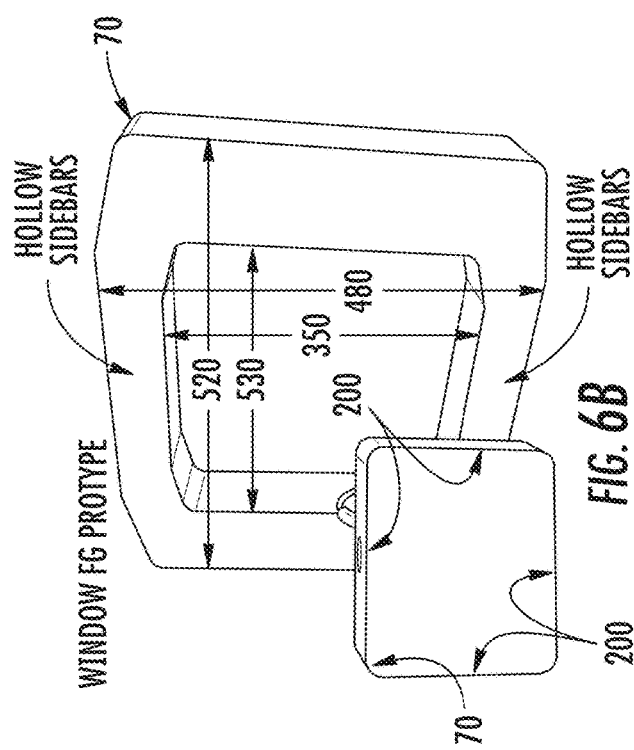
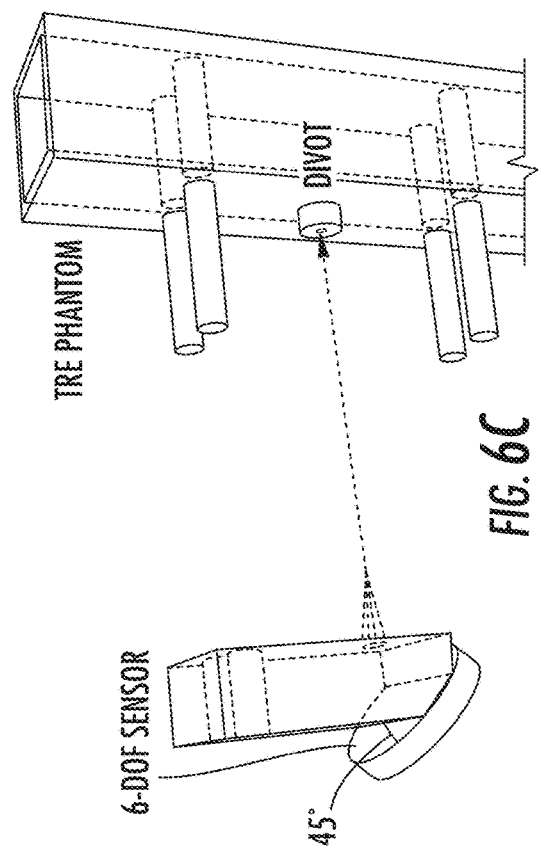
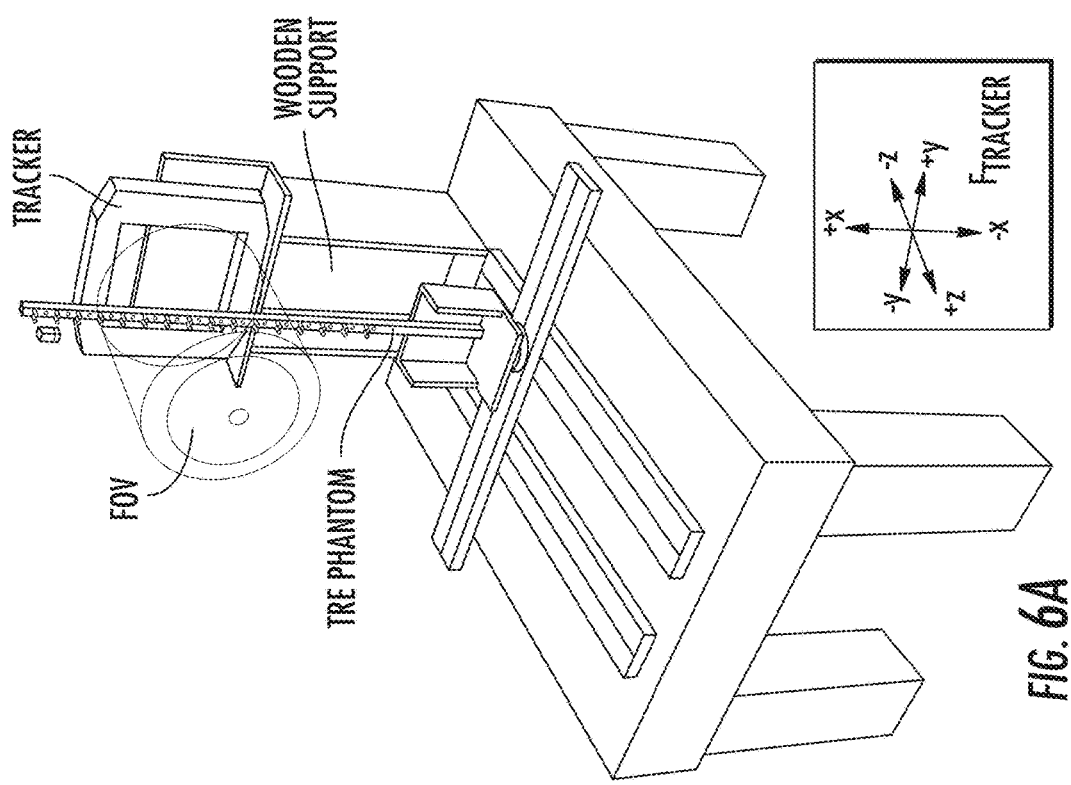
FIG. 6B
FIG. 6C
FIG. 6A

ELECTROMAGNETIC TRACKING SYSTEM AND METHODS OF USING SAME

CROSS-REFERENCE TO RELATED APPLICATIONS

This application is a Continuation of U.S. patent application Ser. No. 14/117,100, filed Aug. 6, 2014, which is a 35 U.S.C. § 371 U.S. national entry of International Application PCT/US2012/037530, having an international filing date of May 11, 2012, which claims priority to U.S. Provisional Patent Application No. 61/485,582, which was filed on May 12, 2011, the content of each of the aforementioned applications is herein incorporated by reference in their entirety.

STATEMENT OF GOVERNMENT SUPPORT

This invention was made with United States government support under Grant CA127444, awarded by the National Institutes of Health. The government has certain rights in this invention.

FIELD

This invention relates to an electromagnetic (EM) tracking system and, more particularly, to an EM tracking system including a patient support element that is superposed relative to an EM field generator.

BACKGROUND

Minimally invasive, image-guided surgery (IGS) offers potential benefits to surgeons and patients alike by providing improved visualization of a surgical target, critical structures surrounding the surgical target, as well as the positioning of instruments used during the surgery, thereby leading to improved surgical accuracy, patient safety, patient recovery, and clinical outcome. Applications of IGS include a wide spectrum of surgical interventions, such as intracranial, head and neck, orthopaedic, spine, and thoracic surgeries. Among the systems enabling next-generation IGS are intraoperative imaging systems, such as mobile C-arms capable of 3D imaging, and guidance systems that register real-time tracking with intraoperative images.

An integral part of IGS is the tracking system. Well known tracking systems include the Polaris Spectra (Northern Digital (NDI), Waterloo, ON Canada), which is based on a stereoscopic infrared camera and retro-reflective markers attached to tracked tools, and the MicronTracker (Claron Technology Inc., Toronto, ON Canada), which is based on a stereoscopic video camera and checkerboard markers. Such systems demonstrate excellent geometric accuracy (about 0.5-2 mm target registration error (TRE)) but suffer potential limitations associated with line of sight obstruction and the inability to track flexible devices within the body. As a result, such optical trackers are typically limited to externalized, rigid tools, such as, for example, rigid pointers and other devices having handles (and markers) that remain outside the body.

The accuracy required in clinical procedures is strongly dependent on the application and surgical site. For example, a previous geometric model has calculated the allowable translational and rotational errors for safe pedicle screw insertion to range from 0.0 mm/0.0° at the T5 vertebra to 3.8 mm/22.7° at the L5 vertebra. The geometric accuracy of tracking systems achieved in practice is typically about 1.5 mm in association with external, rigid tools, such as, for example, rigid pointers or frames. Electromagnetic (EM) trackers provide increased flexibility in tool design due to the use of a small EM sensor and freedom from line-of-sight obstruction. While EM trackers can exhibit somewhat reduced geometric accuracy (about 1-2 mm TRE for the Aurora EM tracking system, NDI) and susceptibility to EM field distortion in the presence of metallic objects, they permit implementations on flexible internal devices (e.g., a bronchoscope) and have shown clinically acceptable accuracy under optimal conditions. Previous studies have examined the influence of specific application settings and the use of specific surgical tools on tracker position and orientation accuracy.

A conventional EM tracker arrangement places an electromagnetic field generator (EMFG) on a mechanical arm over an operating table. The EMFG is draped in proximity to the sterile field. This setup has also been extended to C-arm cone-beam computed tomography (CBCT) by moving the tracker just outside the C-arm field-of-view (FOV). The EMFG typically includes a mass of metallic coils that are not x-ray compatible, necessitating that it be moved during x-ray imaging or positioned out of the x-ray FOV such that the tracker FOV still encompasses the surgical field.

An exemplary setup of a conventional EMFG mounted at tableside is shown in FIG. 1. The setup is shown within the context of x-ray fluoroscopy and/or CBCT. The region of the patient including the surgical target is placed within the FOV ("measurement volume") of the EM tracker (and the fluoroscopy/CT system). The Aurora EMFG is shown (NDI, Waterloo ON), along with an EM tracker control unit, tracked wired tools, two power cables, and a serial communication cable to personal computer (PC).

This conventional EM tracker arrangement has many limitations. First, arranging essential components of the EM tracking system is time-consuming and makes operating rooms complicated—an EMFG, an EM tracker control unit, wired tracked tools, two power cables, and a serial communication cable to PC must be arranged in an operating site so as to avoid other medical equipment. Second, the complicated setup limits intraoperative use of image-guided surgical system—the cables, tripod, and/or support arm needed to hold the EMFG can be incompatible with X-ray fluoroscopy, computed tomography (CT), and/or CBCT when the EMFG is in place. Thus, the EMFG must generally be positioned outside of the X-ray field. Additionally, the conventional position of the EMFG over the table limits space and access to the patient. Further, mounting of the EMFG above the table on a support arm introduces potential sterility challenges—the system must be bagged and protected from non-sterile exposure.

Accordingly, there is a need in the pertinent art for electromagnetic tracking systems and methods that improve space and access to the patient while preserving the sterility of the surgical field. There is a further need in the pertinent art for electromagnetic tracking systems and methods that are compatible with X-ray imaging techniques, thereby permitting intraoperative usage of such systems and methods.

SUMMARY

Described herein is an electromagnetic tracking system. In one example, the electromagnetic tracking system includes a patient support element and an electromagnetic field generator. The patient support element has a longitudinal axis, a transverse axis, and a patient contact surface.

The transverse axis of the patient support table is substantially perpendicular to the longitudinal axis of the patient support element. The electromagnetic field generator is selectively moveable along at least one of the longitudinal axis and the transverse axis of the patient support table. The patient contact surface of the patient support element is superposed relative to at least a portion of the electromagnetic field generator.

In another example, the electromagnetic tracking system includes a patient support table and an electromagnetic field generator. The patient support table has a longitudinal axis, a transverse axis, and a patient contact surface. The transverse axis of the patient support table is substantially perpendicular to the longitudinal axis of the patient support table. The electromagnetic field generator is operatively coupled to the patient support table and is selectively moveable along at least one of the longitudinal axis and the transverse axis of the patient support table. The patient contact surface of the patient support table is superposed relative to at least a portion of the electromagnetic field generator. The electromagnetic field generator has a lower surface and an upper surface.

Optionally, the electromagnetic field generator can define a central opening through the lower surface and the upper surface of the electromagnetic field generator.

Methods of using the electromagnetic tracking system are also disclosed.

BRIEF DESCRIPTION OF THE FIGURES

These and other features of the preferred embodiments of the invention will become more apparent in the detailed description in which reference is made to the appended drawings wherein:

FIG. 4A also depicts an exemplary electromagnetic field generator having a central opening, as described herein, as compared to FIG. 4B a conventional electromagnetic field generator. FIG. 4C illustrates a mobile C-arm in laterior pose.

FIG. 6A is a schematic diagram of the benchtop setup for measurement of the accuracy of the electromagnetic tracking systems, as described herein. FIG. 6B illustrates the shape and dimensions of an exemplary field generator without a central opening (the Aurora FG, NDI) and an exemplary electromagnetic field generator having a central opening (units given in mm). FIG. 6C illustrates a 6 degrees-of-freedom EM sensor mounted on a target registration error (TRE) phantom using rigid posts and a "divot" hole at discrete locations along the x-axis, as described herein.

FIG. 9A was taken at z=134±4 mm; FIG. 9B was taken at z=235±4 mm; FIG. 9C was taken at z=335±4 mm; FIG. 9D was taken at z=436±5 mm; and FIG. 9E was taken at z=538±5 mm. FIG. 9F illustrates the experimental setup and the five "slice" locations.

DETAILED DESCRIPTION

Figure 1:
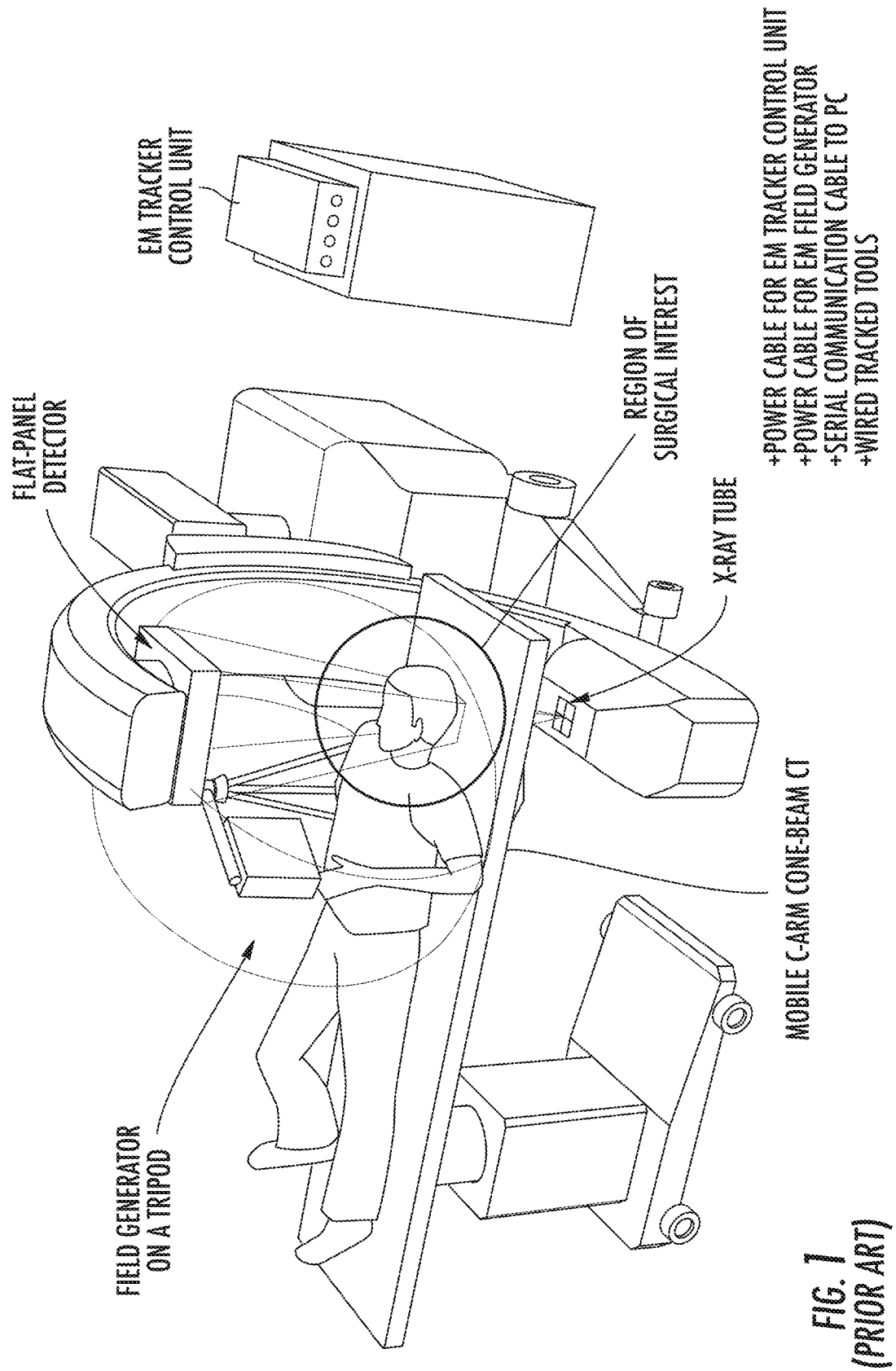
FIG. 1 displays a conventional setup for an electromagnetic tracking system, as used during a C-arm fluoroscopy and/or CBCT procedure.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a splint" can include two or more such splints unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject that is or may be afflicted with a disease or disorder. The term "patient" includes human and veterinary subjects. As used herein, the term "subject" can be used interchangeably with the term "patient."

Disclosed herein are electromagnetic tracking systems and methods that employ an electromagnetic field generator that is positioned beneath a patient, thereby providing improved proximity to a selected region of the patient. As compared to conventional electromagnetic tracking and imaging systems, this arrangement can provide a larger field of view (FOV) during various imaging procedures, including, for example, X-ray imaging and computed tomography (CT) imaging. Exemplary electromagnetic tracking systems, as described further herein, can comprise coils that are arranged along two sides of a rectangular window frame, providing a central opening and substantially hollow side supports, which house small wires connecting the coils. These electromagnetic tracking systems are X-ray compatible in standard fluoroscopic setups, standard computed tomography (CT), and rotational cone-beam computed tomography (CBCT) contexts. Optionally, the electromagnetic field generator can be incorporated into or attached to a surgical operating table, a CT scanner patient support, a radiation therapy patient support ("couch"), or other patient support table. In surgical contexts, these arrangements reduce the amount of equipment that is introduced into a sterile surgical field (above the level of the patient support table) and providing a simpler, more streamlined table-side setup. Some exemplary electromagnetic tracking systems can comprise conventional electromagnetic field generators that are incorporated into a patient support table in this manner. The electromagnetic tracking systems described herein can be used in various applications, including, for example and without limitation, image guided surgeries, radiotherapy treatments, image scanning processes, and the like. As compared to conventional electromagnetic tracking systems, the electromagnetic tracking systems described herein offer a simpler setup, better patient access, more accurate tracking functionality, x-ray compatibility, and easier sterilization.

In one aspect, and with reference to FIGS. 1-5, an electromagnetic tracking system 10 can comprise a patient support element 12. In this aspect, and as shown in FIG. 2A, the patient support element can have a longitudinal axis 14, a transverse axis 16, and a patient contact surface 18. The longitudinal axis 14 of the patient support element 12 can be substantially perpendicular to the transverse axis of the patient support element. In exemplary aspects, the patient support element 12 can be a patient support table, such as, for example and without limitation, a surgical operating table. However, it is contemplated that the patient support element 12 can be any element upon which any portion of the patient is positioned, including, for example, a radiotherapy couch, a scanner bed of an imaging system, and the like.

In another aspect, the electromagnetic tracking system 10 can comprise an electromagnetic field generator 30. In this aspect, the electromagnetic field generator 30 can be selectively moveable along at least one of the longitudinal axis 14 and the transverse axis 16 of the patient support element 12. Thus, it is contemplated that the electromagnetic field generator 30 can optionally be selectively moveable along the longitudinal axis 14 of the patient support element 12. It is further contemplated that the electromagnetic field generator 30 can optionally be selectively moveable along the transverse axis 16 of the patient support element 12. It is still further contemplated that the electromagnetic field generator 30 can optionally be selectively moveable along both the longitudinal axis 14 and the transverse axis 16 of the patient support element 12.

In a further aspect, as shown in FIGS. 2-5, the patient contact surface 18 of the patient support element 12 can be superposed relative to at least a portion of the electromagnetic field generator 30. Thus, in this aspect, it is contemplated that the electromagnetic field generator 30 can be positioned generally beneath the patient support element 12. It is further contemplated that the patient support element 12 can be vertically spaced from the electromagnetic field generator 30 by a selected distance.

It is contemplated that the electromagnetic field generator 30 can be operatively coupled to the patient support member 12. Optionally, in exemplary aspects, as shown in FIG. 2, the electromagnetic field generator 30 can optionally be integrally positioned within the patient support element 12. It is contemplated that the electromagnetic field generator 30 can be configured to move within the table to maintain the field of view on the region of interest (e.g., the "sweet region" in which tracker accuracy is highest) through either selective, manual sliding of the electromagnetic field generator or automated sliding of the electromagnetic field generator through reading the position of a tracked surgical tool. It is further contemplated that sliding of the electromagnetic field generator 30, whether manual or automatic, can be accomplished through the use of conventional motorized systems for effecting longitudinal positioning of a component, including, for example and without limitation, conveyor systems, pressurized valve systems, and the like, which can optionally be operatively coupled to a control unit and/or computer as described herein. It is still further contemplated that integration of the electromagnetic field generator 30 with a tracker control unit, cables, and the like within the table can provide a simpler overall setup with improved sterility considerations and better patient access (when compared to conventional electromagnetic tracking systems).

Figure 2A:
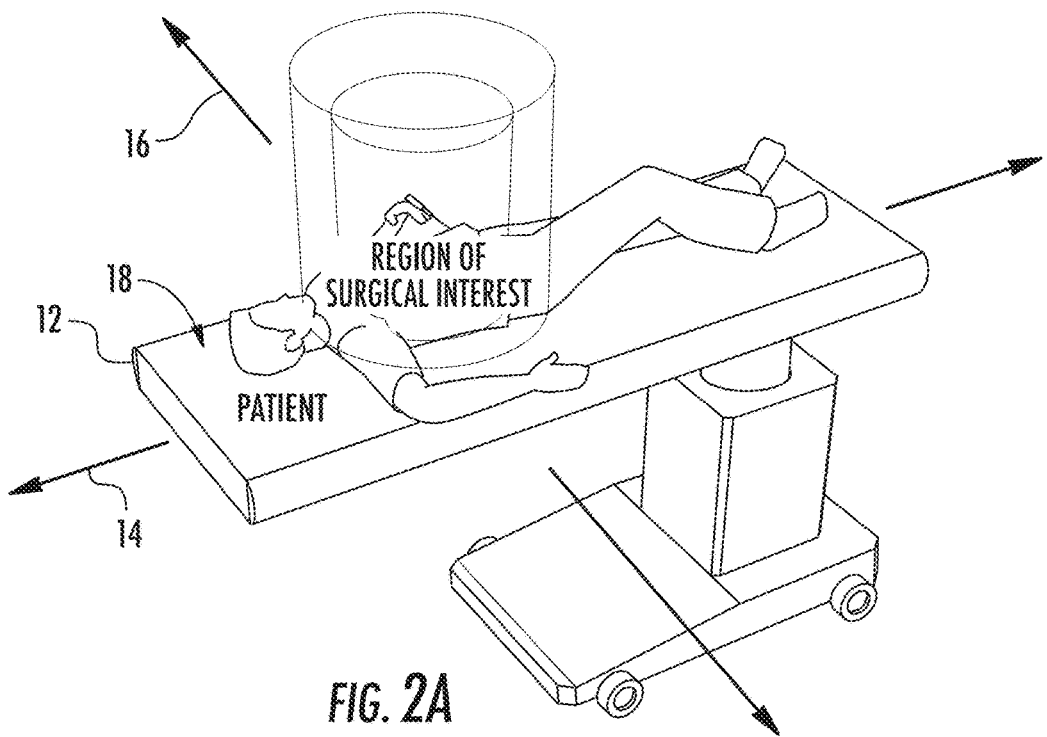
FIG. 2A displays an exemplary patient support table having an integral electromagnetic field generator, as described herein.
Figure 2B:
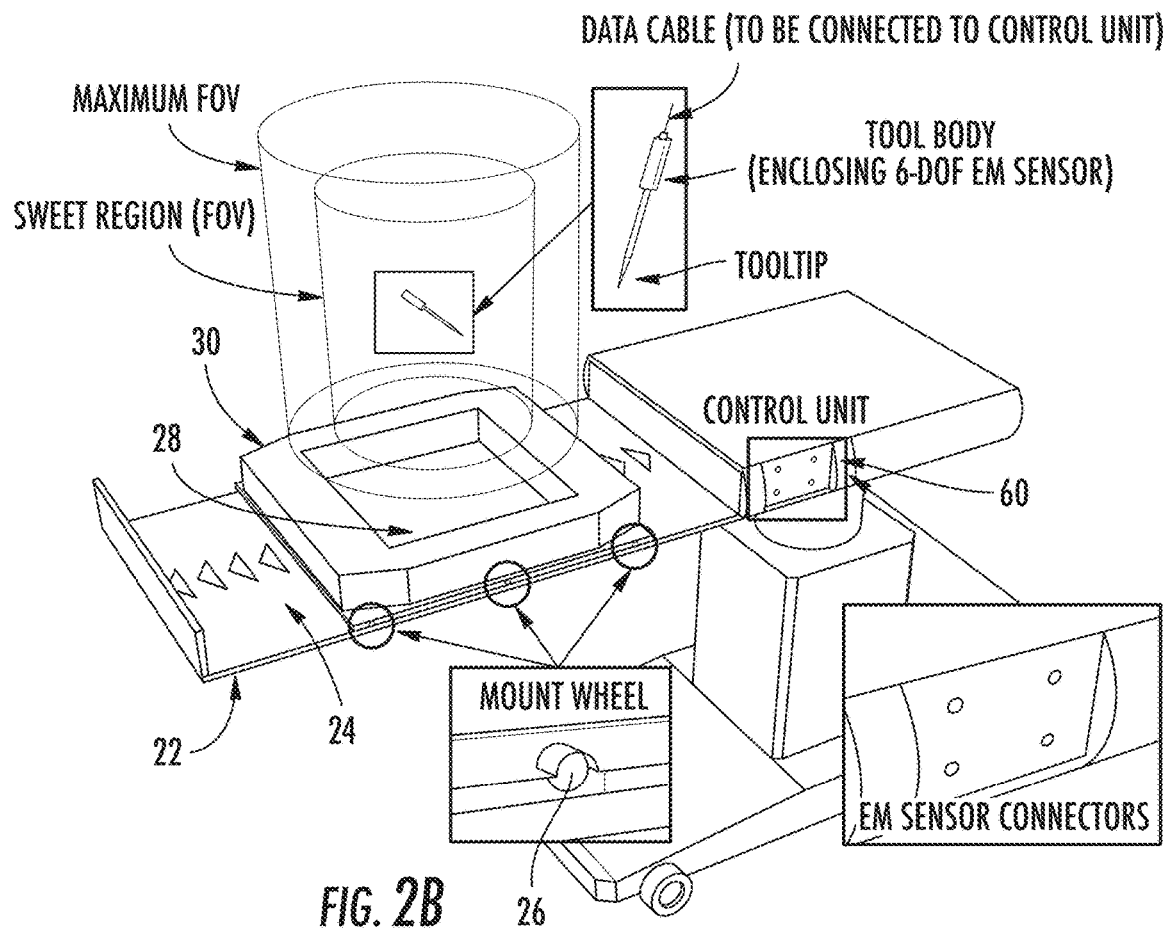
FIG. 2B displays a partial cut-away view of the patient support table of FIG. 2A that schematically depicts the tracking of a surgical tool by the electromagnetic tracking system described herein.

In another aspect, and with reference to FIG. 2B, the patient support element 12 can have an undersurface 22 that cooperates with the patient contact surface 18 to define a hollow compartment 24 that is configured to receive the electromagnetic field generator 30 (such that the electromagnetic field generator is positioned in between the undersurface and the patient contact surface). In this aspect, following receipt of the electromagnetic field generator 30 within the hollow compartment 24, the hollow compartment can be configured to permit sliding movement of the electromagnetic field generator along at least one of the longitudinal axis 14 of the patient support element 12 and the transverse axis 14 of the patient support element 12 and, preferably, can permit sliding movement of the electromagnetic field generator along both the longitudinal axis and transverse axis of the patient support element. It is contemplated that at least one side portion of the patient support element 12 spanning between the patient contact surface 18 and the undersurface 22 can be open and/or configured to provide access to the electromagnetic field generator 30 following positioning of the electromagnetic field generator within the hollow compartment 24. It is contemplated that the electromagnetic field generator 30 can comprise, or be coupled to, a plurality of wheels 26 configured to permit sliding movement of the electromagnetic field generator along the respective axes of the patient support element 12. As shown in FIG. 2B, it is further contemplated that the electromagnetic field generator can be positioned on and/or secured to a mount 28 positioned within the hollow compartment 24 such that movement of the mount effects a corresponding movement of the electromagnetic field generator. The mount 28 can optionally be operatively coupled to the plurality of wheels 26.

Figure 3C:
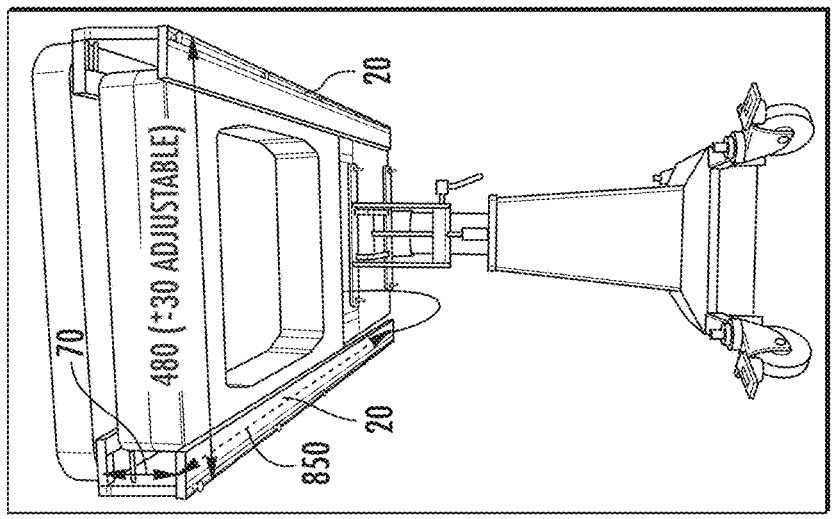
FIG. 3C depicts exemplary dimensions of the patient support table of FIG. 3B, with the dotted line indicating the sliding direction (units given in mm).
Figure 3B:
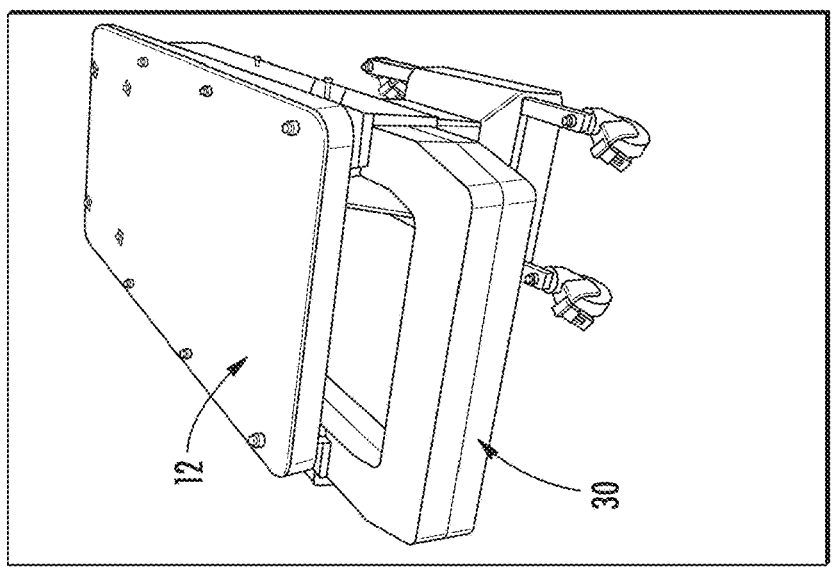
FIG. 3B depicts an exemplary patient support table having a pair of spaced brackets for receiving an electromagnetic field generator, as described herein.
Figure 3A:
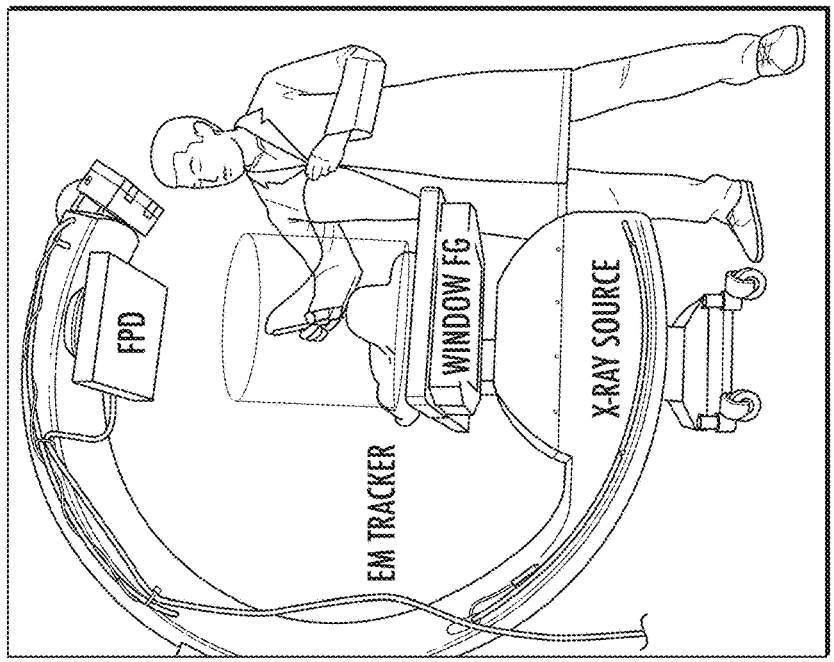
FIG. 3A depicts an exemplary mobile C-arm for intraoperative CBCT that is positioned relative to an electromagnetic field generator having a central opening, as described herein.

In an additional aspect, and with reference to FIG. 3, the patient support element 12 can comprise a pair of spaced brackets 20 that are configured to slidingly receive the electromagnetic field generator 30. Thus, in this aspect, the electromagnetic field generator 30 can be configured to slide within the spaced brackets 20. Optionally, the pair of spaced brackets 20 can extend substantially parallel to the longitudinal axis 14 of the patient support element 12. Alternatively, it is further contemplated that the pair of spaced brackets 20 can optionally extend substantially parallel to the transverse axis 16 of the patient support element 12. In exemplary aspects, it is contemplated that the relative positions of the brackets 20, such as, for example, the space between opposed brackets, can be selectively adjusted. It is further contemplated that the brackets 20 can comprise non-metallic materials, such as, for example and without limitation, acrylic and/or plastic materials, to thereby avoid electromagnetic field distortion and provide x-ray compatibility. For example, it is contemplated that brackets 20 formed of plastic materials will not absorb x-rays, thereby ensuring x-ray compatibility. As used herein, the term "bracket" includes any bracket, rail, or other elongate element defining a longitudinal channel that is configured to slidingly receive an electromagnetic field generator 30, as described herein. It is contemplated that the electromagnetic field generator can comprise, or be coupled to, a plurality of wheels 26 configured to permit sliding movement of the electromagnetic field generator within the brackets 20 along the respective axes of the patient support element 12. Optionally, the electromagnetic field generator 30 can be positioned on and/or secured to a mount 28 positioned within the brackets 20 such that movement of the mount effects a corresponding movement of the electromagnetic field generator. It is further contemplated that the mount 28 can optionally be operatively coupled to the plurality of wheels 26.

Figure 4B:
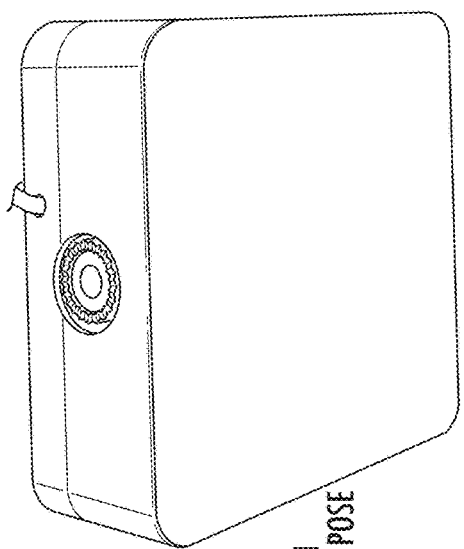
FIGS. 4A-C depict an exemplary electromagnetic tracking system having a mobile C-arm and an electromagnetic field generator for CBCT, as described herein.
Figure 5:
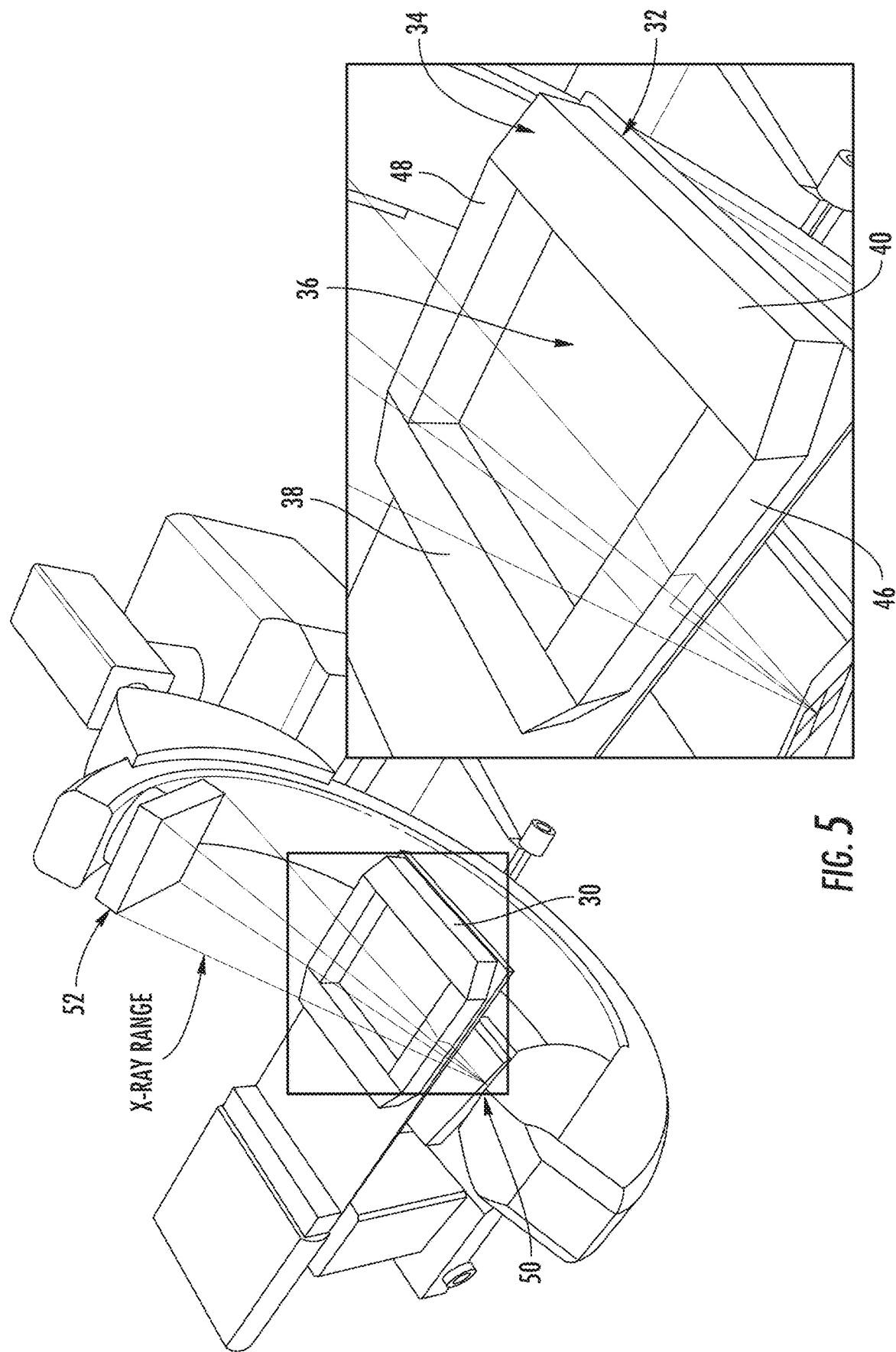
FIG. 5 depicts an exemplary electromagnetic tracking system having a mobile C-arm and a close-up view of an electromagnetic field generator having a central opening, as described herein.

In one aspect, and with reference to FIG. 5, the electromagnetic field generator 30 can have a lower surface 32 and an upper surface 34. In this aspect, the electromagnetic field generator 30 can optionally define a central opening 36 through the lower surface 32 and the upper surface 34 of the electromagnetic field generator. It should be appreciated that, unlike the conventional electromagnetic field generator depicted in FIG. 4B, which is not X-ray compatible due to a mass of metallic materials at the center of the field generator, the central opening can provide X-ray compatibility for the electromagnetic field generator depicted in FIG. 5.

In an additional aspect, it is contemplated that the electromagnetic tracking system 10 can further comprise a releasable locking assembly for securing the electromagnetic field generator 30 in a desired location following selective movement of the field generator along one or more of the axes of the patient support element 12. For example, it is contemplated that the releasable locking assembly can comprise a plurality of screws that can cooperate with the hollow compartment 24 or the brackets 20 to securely lock the field generator 30 in the desired location during an imaging procedure. However, it is contemplated that any conventional means for securing one element in a longitudinal position can be used to secure the electromagnetic field generator 30 in the desired location.

In various aspects, the electromagnetic field generator 30 can comprise a plurality of coils that are spaced so as to permit transmission of radiation through the electromagnetic field generator without contacting the plurality of coils, thereby preserving x-ray compatibility. In one exemplary aspect, the plurality of coils can be spaced about the central opening 36 of the electromagnetic field generator 30. In another exemplary aspect, when the electromagnetic field generator 30 is integrally positioned within the patient support element 12, it is contemplated that the plurality of coils can be spaced about a periphery of the patient support element.

In another aspect, the electromagnetic field generator 30 can comprise a first coil assembly 38 and a second coil assembly 40. In this aspect, the first coil assembly 38 can be in electrical communication with the second coil assembly 40. In exemplary aspects, the first and second coil assemblies 38, 40 can comprise at least one coil. Optionally, in these aspects, the at least one coil of the first and second coil assemblies 38, 40 can comprise a plurality of coils. In a particular exemplary aspect, the first and second coil assemblies 38, 40 comprise a plurality of spaced coils. With reference to FIG. 5, it is contemplated that the first coil assembly 38 and the second coil assembly 40 can both comprise a plurality of coils, with the plurality of coils of the first coil assembly being spaced along an axis substantially parallel to an axis along which the plurality of coils of the second coil assembly 40 are spaced. Optionally, the plurality of coils of the first and second coil assemblies 38, 40 can be spaced along an axis that is substantially parallel to the longitudinal axis 14 of the patient support element 12. Alternatively, the plurality of coils of the first and second coil assemblies 38, 40 can be spaced along an axis that is substantially parallel to the transverse axis 16 of the patient support element 12. It is further contemplated that the first coil assembly 38 can be in opposed spaced relation to the second coil assembly 40 across the central opening 36 of the electromagnetic field generator 30.

In a further aspect, as shown in FIGS. 3 and 5, the electromagnetic field generator 30 can further comprise first and second coil housing arms 42, 44 and first and second side arms 46, 48. In this aspect, the first and second coil housing arms 42, 44 and the first and second side arms 46, 48 can cooperate to define the central opening 36 of the electromagnetic field generator 30. It is contemplated that the first coil assembly 38 can be positioned with the first coil housing arm 42, while the second coil assembly 40 can be positioned within the second coil housing arm 44. It is still further contemplated that the first and second side arms 46, 48 can be connected to and oriented substantially perpendicularly to the first and second coil housing arms 42, 44. In exemplary aspects, the first and second side arms 46, 48 of the electromagnetic field generator 30 can be substantially hollow. It is contemplated that, during an imaging procedures, although the hollow side arms are visible in oblique and lateral x-ray projections, they present fairly low attenuation. In additional optional, exemplary aspects, it is contemplated that the first and second side arms 46, 48 can be formed to have smooth and/or rounded corners, thereby reducing artifact during imaging procedures. In an additional aspect, the first and second side arms 46, 48 of the electromagnetic field generator 30 can comprise plastic materials, thereby avoiding electromagnetic field distortion and providing x-ray compatibility. In exemplary aspects, the side arms 46, 48 can define respective side edges, and at least a portion of the side edges of each side arm can be rounded. In these aspects, it is contemplated that the absence of sharp edges in the electromagnetic field generator 30 can reduce artifact within images obtained using the claimed electromagnetic tracking system 10.

In further aspects, it is contemplated that the electromagnetic field generator 30 can comprise one or more radio-translucent materials. In this aspect, as one will appreciate, the radio-translucent characteristics of the electromagnetic field generator render the electromagnetic field generator suitable for usage with X-ray devices and other radiation sources. In one exemplary aspect, it is contemplated that the electromagnetic field generator 30 can comprise a radio-translucent sheet having a periphery surrounding a central region. In this aspect, it is contemplated that the plurality of coils of the electromagnetic field generator 30 can be spaced about the central region within the periphery of the radio-translucent sheet. It is further contemplated that the spacing of the plurality of coils about the central region can be configured to permit transmission of radiation through the central region without contacting the plurality of coils.

Figure 4C:
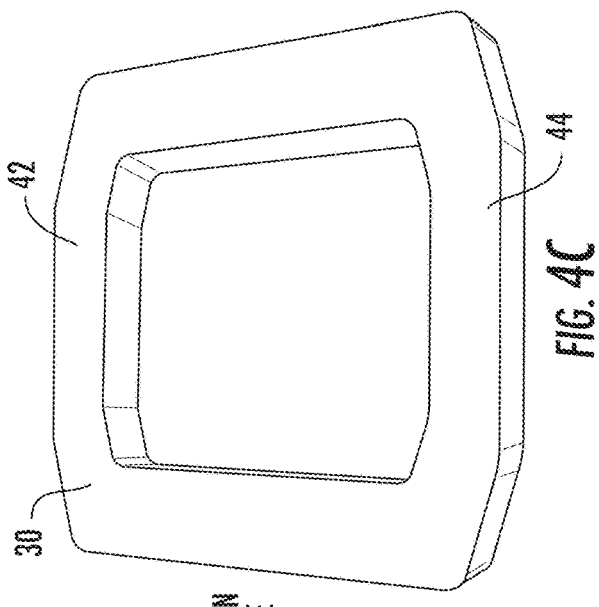
Figure 4A:
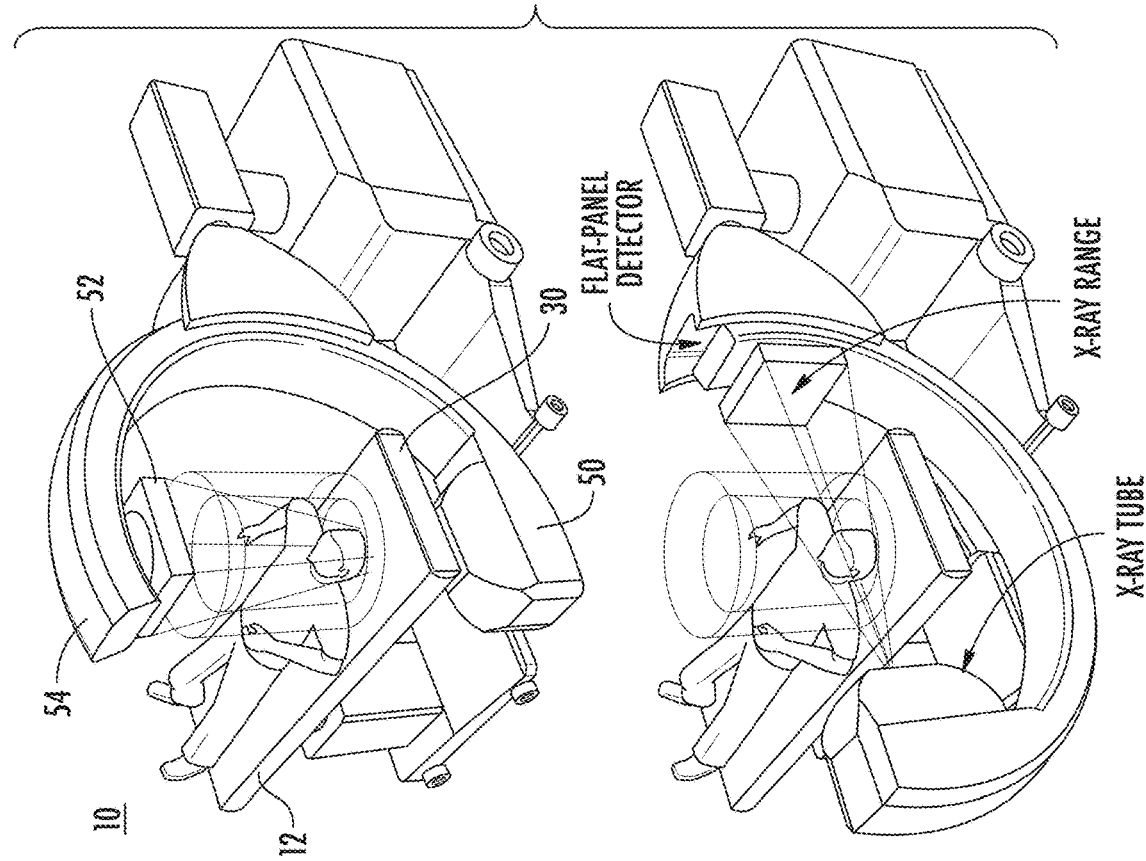

In various aspects, the electromagnetic tracking system 10 can further comprise a radiation source 50, such as, for example and without limitation, an X-ray source, a CT machine, a positron emission tomography (PET) scanner, a radiation therapy treatment system, and the like. Thus, it is contemplated that the radiation source 50 can be an imaging device and/or a therapy device. Optionally, it is contemplated that the radiation source 50 can be configured to selectively transmit radiation toward the patient (such as, for example, in X-ray, CT, or CBCT procedures). It is further contemplated that the radiation source 50 can be selectively positioned such that radiation can be delivered through the central opening 36 and/or the hollow side arms 46, 48 of an exemplary electromagnetic field generator 30, as described herein. In an exemplary aspect, as shown in FIGS. 4A-4C, the radiation source 50 can comprise a detector 52 configured to receive radiation transmitted through the patient and convert the received radiation into an output image. In this aspect, it is contemplated that the detector 52 can be a flat panel detector. However, it is contemplated that any conventional imaging detector can be used in the described electromagnetic tracking system 10. In another aspect, and with reference to FIGS. 4A-4C, the radiation source 50 can further comprise a C-arm, such as those used during conventional X-ray, CT, and/or CBCT procedures.

In an additional aspect, the electromagnetic tracking system 10 can further comprise a control unit 60. In this aspect, the control unit 60 can be in electrical communication with one or more of: the imaging device; the electromagnetic field generator; a computer; a surgical tool, and electromagnetic sensor connectors. In exemplary aspects, as shown in FIG. 2B, it is contemplated that the control unit 60 can be incorporated directly into the patient support element 12.

In an exemplary configuration, the control unit 60 can be in electrical communication with a computer workstation through an interface. The electrical communication between the control unit 60 and the computer workstation can occur through various communication protocols, including, for example and without limitation, Ethernet, serial cable connections, universal serial bus (USB) connections, firewire connections, and/or Bluetooth. It is contemplated that the computer can have a processor that is configured to transmit signals indicative of operation, data sampling, and other information to the control unit 60. It is further contemplated that the computer can be configured to receive signals from the control unit 60 indicative of system operation, timing, and the state, position, and/or orientation of tracked surgical instruments. Optionally, it is contemplated that the control unit 60 can be in electrical communication with the radiation source 50 for purposes of synchronizing the tracking, imaging, and/or treatment operations of the system 10 and/or to direct the operation of the radiation source in response to information received from the computer and/or other elements of the tracking system, such as a tracked surgical instrument.

In use, the electromagnetic tracking system 10 can be used in an electromagnetic tracking method. In one aspect, the electromagnetic tracking method can comprise positioning a patient on the patient support element. In another aspect, the electromagnetic tracking method can comprise positioning the electromagnetic field generator such that the patient contact surface of the patient support element is superposed relative to at least a portion of the electromagnetic field generator. In an additional aspect, the electromagnetic tracking method can comprise positioning an imaging source at a selected orientation relative to the electromagnetic field generator. In this aspect, when the electromagnetic field generator defines a central opening as described herein, the step of positioning the imaging device at the selected orientation can comprise positioning the imaging device such that radiation is selectively transmittable through at least one of (a) the central opening of the electromagnetic field generator and (b) the first and second hollow side arms of the electromagnetic field generator. In a further aspect, the electromagnetic tracking method can comprise selectively activating the imaging device. In still a further aspect, the electromagnetic tracking method can comprise selectively activating the electromagnetic field generator.

Optionally, in an additional aspect, the electromagnetic tracking method can comprise selectively moving the electromagnetic field generator along at least one of the longitudinal axis and the transverse axis of the patient support element. In this aspect, it is contemplated that such movement of the electromagnetic field generator can be accomplished manually. However, in exemplary aspects, it is contemplated that movement of the electromagnetic field generator can occur automatically depending upon the positioning of a surgical tool that is tracked by the electromagnetic tracking system. In these aspects, it is contemplated that the tracked surgical tool can comprise a tool body enclosing at least one electromagnetic sensor. It is further contemplated that the tracked surgical tool can be in electrical communication with the control unit via a data cable such that signals produced by the electromagnetic sensor(s) within the tool body are transmitted to the control unit.

When the electromagnetic tracking system comprises a C-arm, the electromagnetic tracking method can optionally comprise registering the C-arm and tracker coordinate systems (i.e., frames of references $(x,y,z)_{image}$, relating to the radiation source (imaging system), and $(x,y,z)_{tracker}$, relating to the tracking system). It is contemplated that registration of the imaging and tracking systems can permit the position of a tracked instrument (e.g., a surgical device tracked within or about the patient and tracked in $(x,y,z)_{tracker}$) to be related to a corresponding position in the image $(x,y,z)_{image}$. Thus, it is contemplated that a tracked instrument, such as a surgical tool, can be visualized within the context of the image. It is further contemplated that registration of the tracker and image reference frames can follow any of various processes common to surgical navigation. For example and without limitation, it is contemplated that selection of three or more geometric points in the world (tracker) reference frame and the corresponding points in the image reference frame can allow for calculation of the mathematical transformation that relates the position in one reference frame to a corresponding position in the other reference frame. In exemplary aspects, this can be accomplished by placing a tracked pointer at a point in the world (tracker) coordinate system that can be correspondingly localized in the image coordinate system and then repeating this three or more times to compute the transform. Similarly, it is contemplated that a tracked tool can be used to trace a surface in the world (tracker) coordinate system—e.g., the external contour of the patient—and then correlated to the corresponding surface in the image coordinate system by a mathematical registration of surfaces to determine the transform.

It is contemplated that the performance of the electromagnetic tracking system 10 can be affected by the proximity of metallic structures, such as, for example, large surgical instruments, a C-arm, a CT scanner, and the like. To allow more accurate tracker-to-image registration in the presence of such systems about the electromagnetic field generator, it is contemplated that the above-described registration steps can be performed with the system placed in a (fixed) position and/or orientation corresponding to a position and/or orientation that the system would typically placed in during a tracking procedure. In cases where the associated system moves about the electromagnetic field generator (for example, a rotational C-arm), it is contemplated that the registration process can be altered such that a plurality of registrations are performed with the associated system at a plurality of positions and/or orientations about the electromagnetic field generator. In such cases, it is further contemplated that the registration corresponding to any particular position and/or orientation of the system can be determined from either the registration from the position and/or orientation among the plurality of positions and/or orientations that is closest to the current position and/or orientation, or a registration that is interpolated from the plurality to provide an estimate of the registration at the current position and/or orientation. Alternatively, it is contemplated that the plurality of registrations can be processed so as to "average" the location of corresponding points measured during the registration process. For example, it is contemplated that each point can be measured in the world (tracker) coordinate system repeatedly at different positions and/or orientations of the associated system. In this example, it is further contemplated that a representative position for each point (e.g., mean position) can be used to compute the transform to the corresponding points in the image coordinate system.

It is further contemplated that the method steps disclosed above can be employed in various methods of treatment, as well as various methods of imaging. For example, methods of the present invention comprise use of electromagnetic tracking systems disclosed herein with medical and surgical procedures including, but not limited to, computer-assisted therapy (CAT) and computer-assisted surgery (CAS), for example, to navigate anatomical structures and target affected tissue, while minimizing damage to healthy surrounding tissue; dental implantology procedures and treatments; functional endoscopic sinus surgery (FESS) for the removal of unwanted tissue in paranasal sinuses in order to facilitate normal respiration, ventilation, and outflow for the patient; targeting tissue to be removed or treated, while navigating around anatomical structures in order to avoid injury to vulnerable structures; integration of robotics into medical and surgical procedures; precisely locate and operate within and around the brain; orthopedic implants, orthopedic treatments and surgical procedures for repair and removal; acquisition of PET (positron emission tomography) information and usage; IGRT (image guided radiation therapy); soft tissue applications such as needle biopsy, fine needle aspiration biopsy (FNAB); spinal surgery, ultrasound therapy and treatments, and transcranial magnetic stimulation (TMS) to trigger brain activity through the use of rapidly changing magnetic fields, for example, in treating severe depression, mania, or auditory hallucinations (e.g. associated with schizophrenia).

In exemplary aspects, the electromagnetic field generator having a central opening as described herein can comprise a Window FG (WFG, manufactured by NDI). However, it is contemplated that any electromagnetic field generator having a central opening and/or having consistently radiotranslucent characteristics throughout its main body (e.g., central and lateral portions) as described herein can be used within the disclosed electromagnetic tracking systems and methods.

It is contemplated that conventional EM field generators, such as, for example and without limitation, the Aurora FG or table-top FG (NDI), can be employed in the disclosed electromagnetic tracking systems and methods. However, it should be appreciated that such conventional EM field generators, which lack a central opening and radio-translucent characteristics, would confound many imaging procedures, including posterior-anterior anterior (PA) fluoroscopy, a fairly large range of oblique views, CT, CBCT, PET, and radiation therapy. Nonetheless, it is contemplated that positioning of conventional EM field generators within a tracking system as described herein can achieve improvements in at least accuracy and field of view.

It is contemplated that the disclosed apparatus and methods can include various components and features described in U.S. Pat. Nos. 7,103,931, 7,609,062, and U.S. Patent Publication No. 2011/0224537, the disclosures of which are hereby incorporated herein by reference in their entirety.

EXPERIMENTAL EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

Example 1

The geometric accuracy (target registration error, TRE) of an exemplary electromagnetic tracking system including a field generator having a central opening as described herein was compared to a conventional EM tracker without a central opening. Additionally, the x-ray compatibility of the exemplary electromagnetic tracking system in combination with a mobile C-arm for cone-beam CT (CBCT) was analyzed. Further, the improvement in workflow associated with the incorporation of the field generator within a patient support table of the electromagnetic tracking system was examined.

TRE was measured for the Window FG and conventional Aurora FG using the testbench in FIG. 3 for precise translation/rotation of a 6-DOF sensor (#610022) and registration phantom throughout the FOV. Although the bench and positioners were metallic, the trackers were mounted at a height of about 100 cm to minimize EM field distortion. Angular dependence in TRE was observed for the 6-DOF sensor, so measurements were performed with the sensor at about 45° to the cardinal axes. In addition, the sensor "indicator value" was recorded for each measurement to assess variability and EM field distortion. Measurements were performed with and without a carbon-fiber plate over the tracker to simulate enclosure within a carbon-fiber OR table. As illustrated in FIG. 1(b), the registration phantom consisted of an acrylic rod and array of divots translated across the bench. The phantom was CT scanned at high-resolution (0.6×0.6×0.3 mm$^3$), with each divot localized in 3D visualization software (±0.1 mm) to establish ground truth. Registration between the phantom and positioning system used fiducials distinct from the defined target divots. The 6-DOF tooltip was pivot-calibrated with tooltip offset error±0.56 mm. Measurements were performed in coarse increments (100 mm) throughout the full FOV and finer increments (25-50 mm) along the central axes.

The Window FG was incorporated in a carbon-fiber OR table as shown in FIG. 3 to assess compatibility with fluoroscopy and CBCT. A prototype C-arm for high-quality CBCT was used. Quantitative test phantoms for image contrast, noise, and resolution were employed, along with an anthropomorphic head/body phantom. Fluoroscopic compatibility was assessed as the range over which the EM field generator with the central opening allowed an unattenuated beam to pass through the opening, including high-mag, isocentric, and low-mag C-arm positioning. CBCT compatibility was assessed in images acquired with and without the central opening in the carbon-fiber table, characterized in terms of truncation artifacts (noise and streaks) from out-of-field attenuation by the tracker.

An expert surgeon provided feedback regarding the integrated tracker-in-table concept in various application procedures, and potential advantages were assessed in comparison to a conventional over-table mount. The influence of metallic tools and C-arm was assessed, and using the sensor indicator value to communicate inaccuracies within navigation software was investigated. Novel hybrid tracker configurations included use of the Window FG with infrared and/or video-based trackers.

Figure 8A:
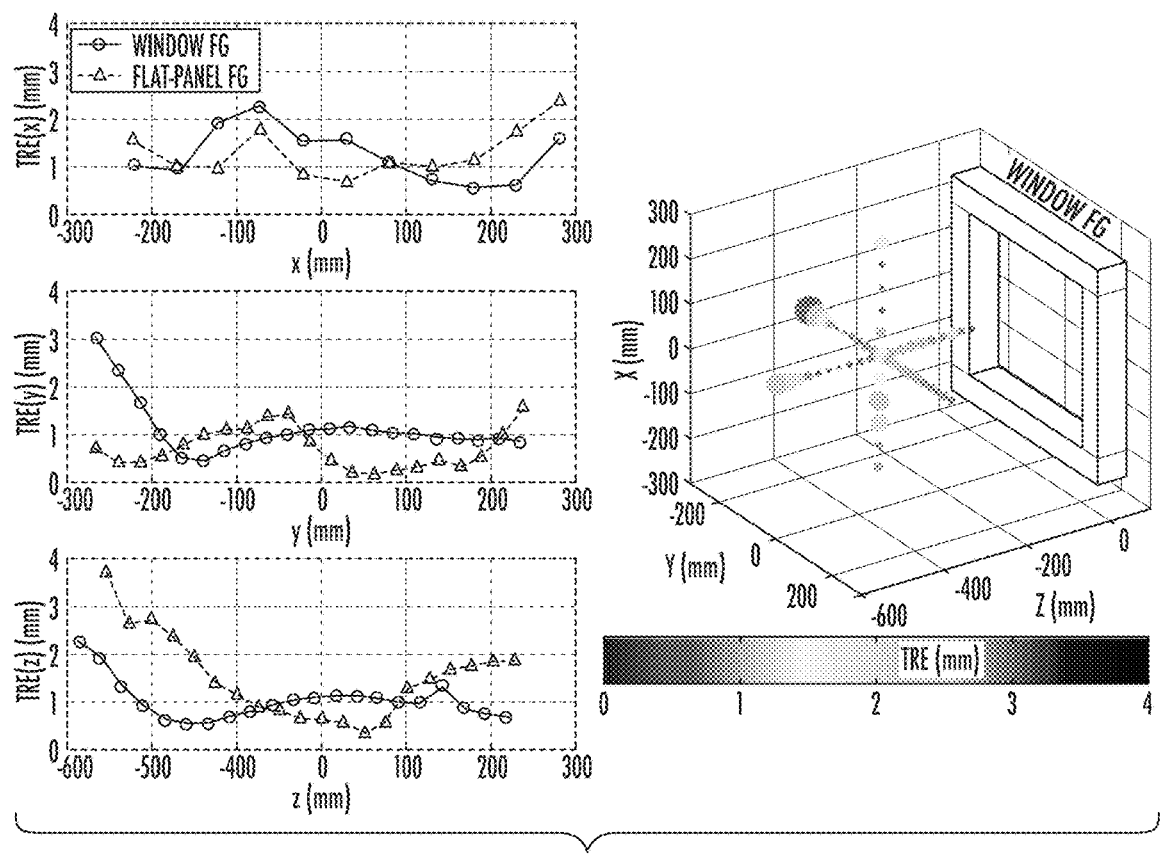
FIG. 8A displays an experimental measurement of TRE across the field of view (FOV) of an exemplary electromagnetic field generator having a central opening as described herein.

The fiducial registration error (FRE) between fiducials on the vertical phantom and divot targets was (1.12±0.39), (1.19±0.59), and (1.30±0.91) mm in (x,y,z) directions for the EM field generator having the central opening, respectively, and (1.49±0.63), (0.96±0.44), (2.33±1.70) mm for the conventional EM field generator (Aurora FG, NDI). As shown in FIG. 8(a), the TRE measured from 10 repeat localizations was (1.43±0.77), (1.29±0.89), and (1.19±0.71) mm in (x,y,z) directions for the EM field generator having the central opening, respectively, and (1.28±0.51), (0.77±0.48), (1.49±0.86) mm for the conventional EM field generator. A slight increase in TRE was observed for the EM field generator having the central opening near one FOV boundary (−y), and the EM field generator having the central opening exhibited superior TRE at greater depth (z). Overall, the magnitude and trend in TRE was similar for each tracker, with the EM field generator having the central opening exhibiting slightly improved accuracy and FOV. There was no change in TRE measured with and without a carbon-fiber plate.

Figure 8B:
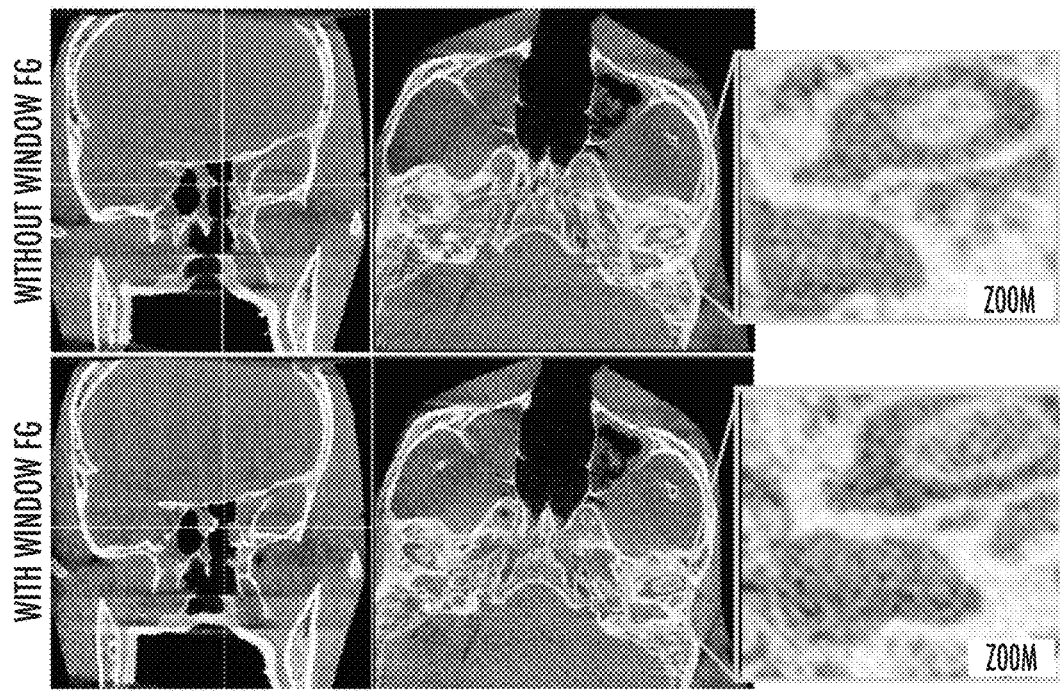
FIG. 8B displays CBCT images obtained without any field generator in the X-ray field (top image) and with the exemplary electromagnetic field generator (with central opening described herein) incorporated in a patient support table (bottom image).
Figure 9A:
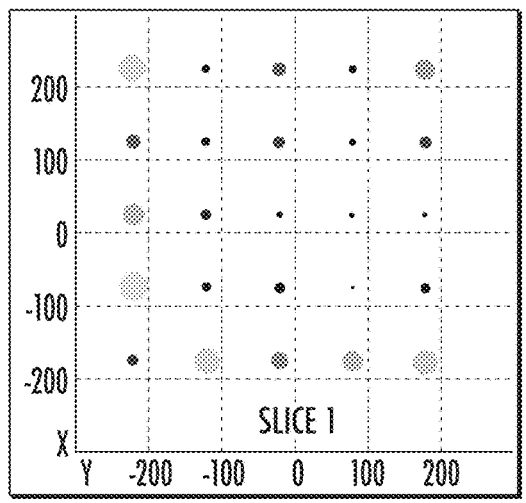
FIGS. 9A-9F depict an experimental measurement of TRE across the FOV of an exemplary electromagnetic field generator at five "slice" locations in the z-direction (away from the field generator). The color and diameter of each circle represent the magnitude of the TRE. Each plot shows the TRE in (x,y) "slices" at various depths (z).
Figure 9B:
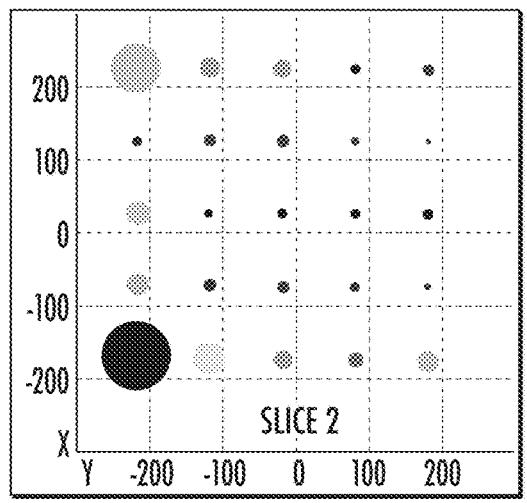
Figure 9C:
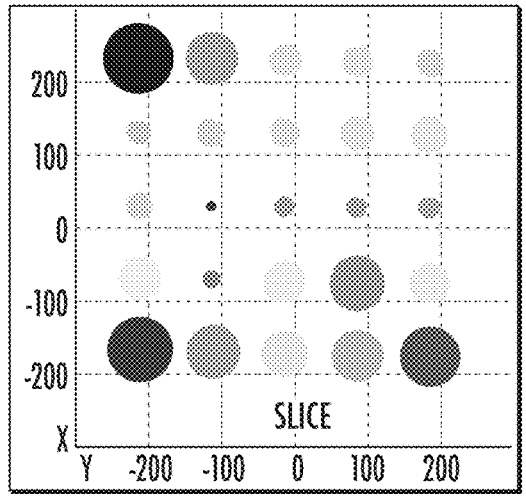
Figure 9D:
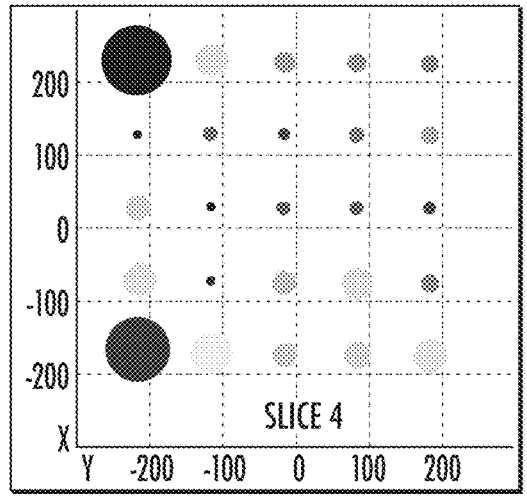
Figure 9E:
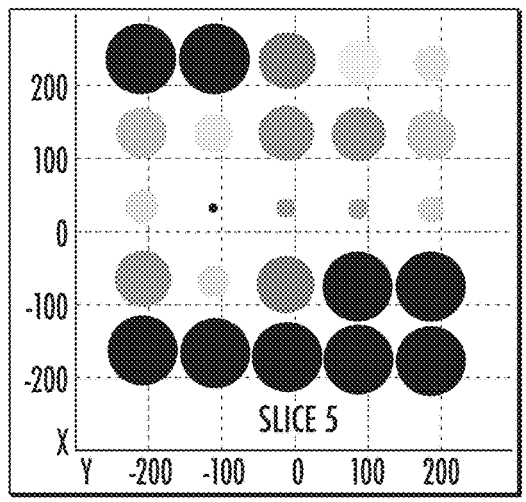
Figure 9F:
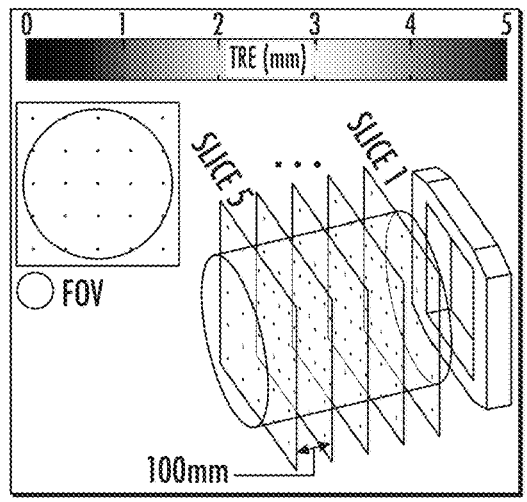

The central opening of the EM field generator was sufficiently large for unattenuated PA fluoroscopy at any level of magnification for the 30×30 cm$^2$ detector. CBCT images acquired without and with the central opening under the OR table are shown in FIG. 8(b). Although the FG enclosure was visible in oblique projections, and only a simple (Gaussian extrapolation) truncation correction was applied, truncation artifacts arising from the EM field generator having the central opening were minimal. A subtle increase in streak artifact is detectable, but the increase in image noise was minimal (~±2-5 HU) at the level of quantum noise.

Expert surgeon feedback suggested a potentially important role for the tracker-in-table concept. The feedback noted clear logistical advantages and x-ray compatibility compared to a conventional over-table mount.

Example 2

2.1 Electromagnetic Trackers

An exemplary EM field generator having a central opening was evaluated in comparison to a conventional Aurora Field Generator (AFG, NDI) in terms of tracking accuracy and FOV. As illustrated in FIG. 5, the exemplary EM field generator presents a large, central opening (about 33×35 cm$^2$) through which the x-ray beam may pass without attenuation (e.g., in a PA view), compared to the compact (and non-radio-translucent) configuration of the AFG. The hollow sidebars of the exemplary EM field generator contained only three thin wires (in one sidebar only), with the sensor coil components enclosed in the bars positioned outside the x-ray beam. This setup gave a high level of x-ray compatibility for a large solid angle about the exemplary EM field generator, with electromagnetic components of the tracker lying outside the x-ray FOV and only the (nearly hollow) sidebars presenting in x-ray projections from the semi-circular orbit of a rotational C-arm.

Figure 7:
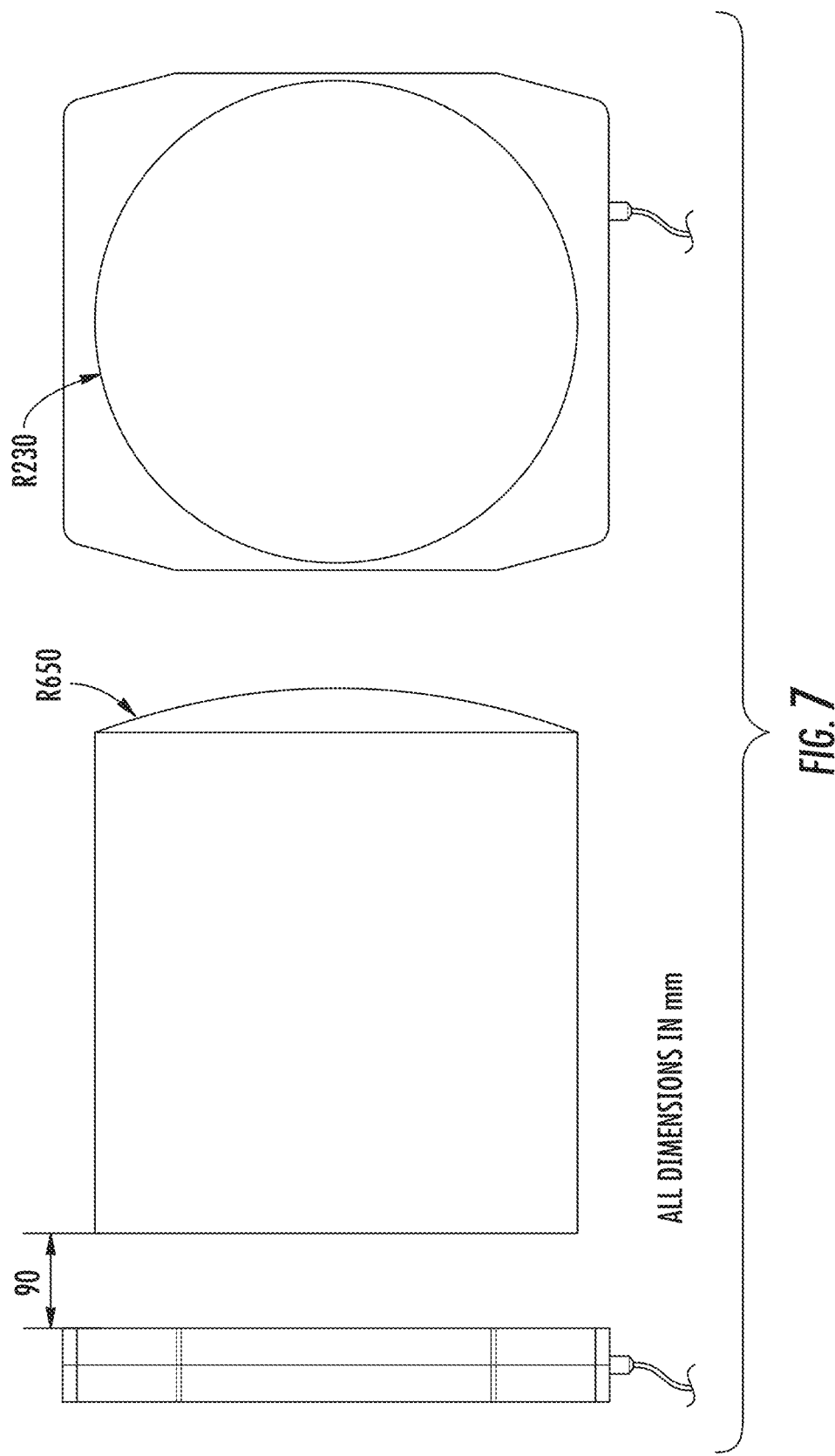
FIG. 7 displays the dimensions of an exemplary electromagnetic field generator having a central opening as described herein.

The current version of the AFG provides two preconfigured selections in FOV—a cube [500 mm side length, about 0.48 mm RMS geometric accuracy (for a 6 DOF (degrees of freedom) sensor)] and a cylindrical dome [960 mm diameter, 660 mm depth, about 0.7 mm RMS geometric accuracy (6 DOF sensor)]. Stated RMS values have been supplied by the manufacturer. Both FOVs include an offset of the trackable area of 50 mm. The cube and dome FOV configurations have similar geometric accuracy in proximity to the FG, and the specified values refer to the average over the entire FOV. The nominal FOV provided by the EM field generator having the central opening is a cylindrical dome (460 mm diameter, 650 mm depth including 90 mm FOV offset from tracker) (see FIG. 7), and initial characterization of geometric accuracy was estimated to be 0.4 mm RMS (6 DOF sensor). FIG. 6(b) gives an example of the dimensions of both tracker embodiments.

FIG. 3 displays (a) the initial experimental configuration of the exemplary EM tracking system including the EM field generator having the central opening, (b) the prototype Tracker-in-Table incorporating the EM field generator beneath a carbon-fiber OR tabletop, and (c) dimensions of an exemplary under-table mount, the dotted line indicates the sliding direction (unit: mm).

2.2 Geometric Accuracy of the WFG and AFG

A precise and reproducible linear positioning bench was built to allow measurement of TRE throughout the tracker FOV in an EM-compatible environment. The measurement bench consisted of two linear translation stages, a 360-degree rotary table, and a custom TRE phantom (See FIG. 6A). The two linear translation stages allowed adjustment of position along the y- and z-axis, and the TRE phantom itself provided adjustment of position along the x-axis. The sensor exhibited a directional dependence in measurements of TRE measured with the EM sensor. All measurements reported below corresponded to a (1,1,0) angulation of the sensor (i.e., 45-degrees about the x and y axes) chosen as representative of an "average" pose in routine use and minimizing bias in measurements in different directions (See FIG. 6C). The 360-degree rotary table was positioned in addition to the hand-driven linear tables to adjust the orientation of the custom-built tool (45 degrees about the x axis). The linear table assembly had a specified precision of 0.1 mm, and the rotary table was specified to a precision of 0.1 degree. A non-metallic (particle board) tracker support was built to elevate the entire FG approximately 80 cm above the surface of the bench to avoid field distortion from the (metallic) benchtop. The TRE phantom was built from non-metallic materials (acrylic and polyethylene) to avoid distortion of the EM field. The phantom included sixteen divots along the x-axis for TRE measurement and sixteen pairs of bars for reproducible positioning of the EM sensor plug (See FIG. 6C). The EM sensor was a 6 DOF Standard Reference Marker provided by the manufacturer consisting of two embedded 5 DOF sensors, showing improved tracking accuracy compared to a single 5 DOF sensor. The sixteen divots were attached at 5 cm spacing in a co-linear manner along the x-axis. Four mounting holes on the inferior plate of the TRE phantom were precisely manufactured to fit with the four mounting holes on the rotary table. A computed tomography (CT) scan of the TRE phantom was acquired (0.64× 0.64×1.00 mm³), and divots were localized to sub-voxel accuracy (~0.1 mm) for the four mounting holes by repeat localization (six times averaged) and tri-planar slice interpolation in the image guidance system. Point-based registration was performed to register the CT scan of the TRE phantom (reference frame—$F_{CT}$) to the lower mounting holes on the bench assembly using the physical position of the four mounting holes of the TRE phantom matching those on the rotary table ($F_{Stage}$). Following point-based registration, the relationship between the tracker measurements in the CT reference frame and the stage coordinates (alternatively referred to as the world coordinate system) could be determined as:

$$F_{Stage} = T_{Stage}^{CT} \cdot F_{CT},$$

where $T_{Stage}^{CT}$ defines the transformation matrix between position vectors in the two reference frames.

To determine the correct position of the tracker measurements in the world coordinate system, it was necessary to add or subtract an offset corresponding to the benchtop assembly to the coordinates of each divot obtained in $F_{CT}$ and transformed to $F_{stage}$. Writing the $i^{th}$ divot measurement on the TRE phantom as $\vec{d}_{CT}^{\,i} = (x_i, y_i, y_i)$, its physical position, $\vec{i}_{Stage}$ was obtained as:

$$\vec{i}_{Stage}^{\,i} = T_{Stage}^{CT} \cdot \vec{d}_{CT}^{\,i} + \vec{\alpha}_{Stage},$$

where $\vec{\alpha}_{Stage}$ is a three-dimensional $$\vec{\alpha}_{Stage} = \begin{bmatrix} 0 \\ \Delta y \\ \Delta z \end{bmatrix}.$$

and $\Delta y$ and $\Delta z$ denote adjustments of the linear slider in y and z directions.

Therefore, for each measurement location two corresponding points were determined: a physical measurement of the sensor tip position and the position of the sensor tip in the image guidance software. Through the established transformation matrix, the points can be moved into a common reference frame and TRE expressed as the Euclidian distance between the points.

FIG. 6(a) provides a schematic of the benchtop setup for measurement of tracker accuracy. The exemplary EM field generator having the central opening and the AFG were placed on a non-metallic (wooden) support, which was mounted to a precise 3D positioning table. Linear stages allowed localization of the 6 DOF EM sensor plug throughout and beyond the tracker FOV. The linear table assembly enabled y- and z-axis motion, and the TRE phantom provided positioning of a pointer in divots along the x-axis in the tracker coordinate system. FIG. 6(b) illustrates the shape and dimensions of the Aurora FG (front left) and the EM field generator having the central opening (back right, unit: mm). FIG. 6(c) illustrates the 6 DOF EM sensor mounted on the TRE phantom using rigid posts and a "divot" hole at discrete locations along the x-axis. The sensor was attached to a connector plate at a 45° angle, giving an intermediate pose approximating freehand use (not aligned with any particular axis). The connector plate included a conical pointer that fit tightly into the "divot" holes, and two through holes that fit the TRE phantom on rigid posts on the x-axis upright. This setup provided reproducible placement of the 6 DOF sensor.

2.3 Implementation of the WFG in a Preclinical C-Arm OR Setup 2.3.1 Prototype OR Table A Tracker-in-Table configuration was implemented as illustrated in FIG. 3. A custom carbon fiber OR tabletop (CFI Medical Solutions, Fenton, Mich. USA) was mounted to a 3-DOF metallic OR table base. The influence of the carbon fiber table on tracking accuracy was found to be negligible (<0.1 mm) by repeating TRE measurements with and without the tabletop on the bench. The custom OR table included acrylic rails attached underneath to support the EM field generator having the central opening. The rails (each 70 mm×850 mm at 480 mm separation) were built from acrylic plates and plastic screws to avoid EM field distortion. The rails allowed width adjustment and (manual) longitudinal positioning of the exemplary EM field generator under the table with set-screws to fix the field generator in a desired position.

2.3.2 Tracking Accuracy in the Presence of a Mobile C-Arm

The tracking accuracy of the EM field generator having the central opening in the Tracker-in-Table prototype was evaluated in the context of C-arm CBCT-guided surgery. The setup included an anthropomorphic chest (The Phantom Laboratory, Greenwich, N.Y. USA) placed in prone position (FIG. 1a). Conical divots drilled on the phantom surface were used separately as registration fiducials (for image-world registration) and target points (for measurement of TRE). The tip of the EM pointer tool (Aurora 6 DOF straight tip pointer tool, 65 mm long, 3 mm diameter) gave a tight fit to the divots, allowing reproducible positioning of the tool tip, and the conical divots were easily discerned in CT images. A distinct set of surface divots was used as target points in measuring TRE. The divots allowed reproducible positioning of the pointer tool tip and could be easily discerned in CT images. In total, 36 divots on the phantom were selected for measurements—9 selected for purposes of image-world registration and 27 selected as target points for analysis of TRE. The 9 registration points were selected as the set (over all possible combinations) that minimized target registration error. The phantom allowed implantation and removal of thoracic and lumbar pedicle screws. The prototype mobile C-arm for CBCT was developed in collaboration with Siemens Healthcare as described in previous work. It is based on an isocentric mobile C-arm (Powermobil, Siemens, Erlangen, Germany) modified to include a large-area flat-panel detector (PaxScan 3030+, Varian Imaging Products, Palo Alto Calif.), a motorized orbital drive, a method for geometric calibration, and a computer control system for image acquisition and 3D reconstruction. The C-arm provides a volumetric FOV ($\sim$15×15×15 cm$^3$) with sub-mm 3D spatial resolution, soft-tissue visibility, and generation of CBCT images ($512^3$ or $256^3$) within $\sim$15 seconds after completion of a scan. The prototype mobile C-arm has been evaluated in the context of orthopaedic (spine) surgery, focusing on image quality and radiation dose in image-guided procedures; cochlear implant; sinus and skull-base surgery, focusing on improved surgical precision in tumor surgery adjacent to critical structures; thoracic surgery, brachytherapy; and guidance of tibial plateau fracture reduction. Stationary C-arms are entering broad use in cardiovascular interventions.

The geometric accuracy of the EM field generator having the central opening was assessed in five distinct scenarios: 1.) without the C-arm and without spine screws; 2.) without the C-arm but with three spine screws in the phantom; 3.) with the C-arm in Lateral (LAT) orientation and with three spine screws in the phantom; 4.) with the C-arm in Posterior-Anterior (PA) orientation and without spine screws in the phantom; and 5.) with the C-arm in PA orientation and with three spine screws in the phantom.

2.3.3 Effect of the EM Field Generator Having the Central Opening on CBCT Image Quality CBCT image quality can be degraded by objects located outside the volumetric FOV, typically in the form of streaks artifacts. The EM field generator having the central opening is located outside the CBCT FOV and it presents fairly low attenuation, and was therefore anticipated to have fairly small effect on 3D image quality. The influence of the EM field generator having the central opening on CBCT image quality was assessed in quantitative and qualitative phantoms. All scans were at the nominal technique previously identified for thoracic scanning: 100 kVp, 230 mAs, and 200 projection images, corresponding to 4.61 mGy dose at the center of a 32 cm body phantom.

Quantitative evaluation involved a QRM Thorax Phantom (Quality Assurance in Radiology and Medicine GmbH, Erlangen, Germany). The phantom was customized to allow placement of an acrylic cylinder containing four tissue-equivalent inserts in the middle of the phantom. The 10 cm acrylic cylinder holder has an electron density relative to water of $\rho_e$=1.15 and approximately 130 HU, and the tissue-equivalent inserts included: solid water ($\rho_e$=0.99, 0 HU), breast ($\rho_e$=0.96, −41 HU), liver ($\rho_e$=1.07, 83 HU), and adipose ($\rho_e$=0.93, −84 HU), each having a diameter of 28 mm (Gammex RMI, Madison Wis.). Soft tissue CNR was measured to compare CBCT image quality with and without the Tracker-in-Table. The contrast (signal difference) was given by the difference in attenuation coefficient between a structure of interest and the background, and the noise was given by the standard deviation in voxel values. The CNR is therefore:

$$CNR = \frac{|\mu_I - \mu_B|}{(\sigma_I + \sigma_B)/2},$$

where $\mu_I$ and $\mu_B$ denote the average voxel value in material "I" (i.e., the structure of interest—for example, a given soft-tissue insert in the QRM phantom) and the background "B" (e.g., the acrylic holder in the QRM phantom). Similarly, $\sigma_I$ and $\sigma_B$ denote the standard deviation in voxel values within the insert and background, respectively.

Qualitative evaluation involved the anthropomorphic chest phantom with spine screws in place (viz., a translaminar screw (T1) and two pedicle screws (T5 and T7)). The spine screws were composed of metal (titanium and steel), which in themselves are expected to produce CBCT image artifacts separate from the out-of-field truncation artifacts possibly introduced by the Tracker-in-Table. The effects on image quality (i.e., CBCT images of the phantom with spine screws, imaged with and without the EM field generator having the central opening in the table) and workflow were assessed qualitatively by an experienced and fellowship-trained spine surgeon.

3. Results 3.1 Geometric Accuracy

For both (a) the EM field generator having the central opening and (b) the AFG tracking systems, the FOV was evaluated first by measuring TRE in coarse increments of 10 cm in (x, y, z). A total of (5×5×5) such measurements were made across about (50×50×50) cm$^3$ and repeated ten times, averaged, and transformed into reference frame $F_{Stage}$ for evaluation of TRE. The measurements (n=250) were performed using a pointer tool calibrated prior to data acquisition. The distance between the measured and actual pointer position included possible (likely small) pointer calibration errors in the resulting TRE, so the reported values may represent a small overestimate of the actual TRE associated with just the tracker (independent of the pointer calibration error). As shown in FIG. 9, the TRE varied across the FOV, most notably in the z (depth) direction. For the EM field generator having the central opening, the TRE (as a function of z) was: 0.91±0.52 mm (at z=134±4.1 mm); 1.00±0.51 mm (at z=235.1±4.1 mm); 1.50±0.64 mm (at z=335.3±4.3 mm); 2.45±0.93 mm (at z=436.0±4.5 mm); and 3.66±1.56 mm (at z=537.5±5.1 mm). Overall, the measurements show a trend of gradually increasing TRE at greater depth, with a mean TRE across the evaluated FOV of 1.90±1.38 mm. Although the farthest measurement was inside the specified FOV, the TRE was seen to increase steeply at the FOV boundaries. Similar evaluations performed for the AFG showed a mean TRE of 2.17±1.91 mm. Statistical analysis on the results, using Student's t-test, showed no significant difference between the EM field generator having the central opening and the AFG (p=0.32).

Figure 10:
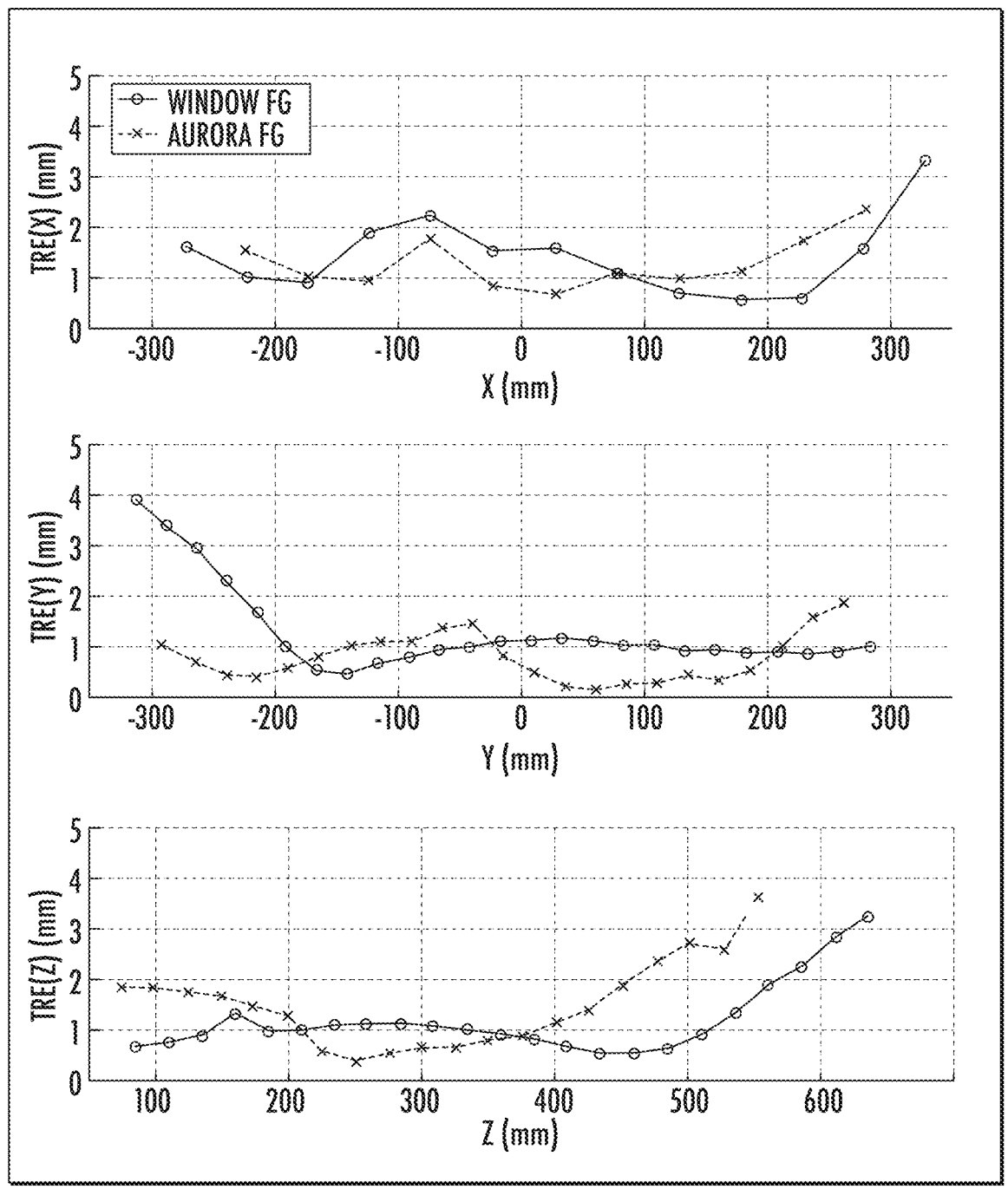
FIG. 10 displays an experimental comparison of TRE along x, y, and z-axes between an electromagnetic field generator that lacks a central opening and an exemplary electromagnetic field generator that has a central opening as described herein.

Measurement of TRE at finer increments in x, y, and z was performed at 2.5 cm increments on the central y-axis and z-axis, and at 5 cm spacing on the central x-axis for both the EM field generator having the central opening and the AFG, each measured ten times. Results are summarized in FIG. 10. The mean TRE along the x-axis for the EM field generator having the central opening was 1.43±0.77 mm, compared to 1.28±0.51 mm for the AFG. The mean TRE along the y-axis of the EM field generator having the central opening was 1.29±0.89 mm, compared to 0.77±0.48 mm for the AFG. The measurements showed an anomalous, gradual increase in TRE for the EM field generator having the central opening near one FOV boundary (−y), increasing from −0.5 mm to −3.9 mm within −150 mm of the FOV edge. The gradual increase was contrary to the sharper increase in TRE at the FOV edge seen for the +x direction [FIG. 10]. Discussions with the manufacturer suggested a small error in the internal calibration of the prototype as a possible explanation, and one that could be rectified by factory recalibration. The mean TRE along the z-axis was 1.19±0.79 mm for the EM field generator having the central opening and 1.13±0.72 mm for the AFG. As summarized in FIG. 5, the overall TRE was slightly improved for the AFG, although the EM field generator having the central opening demonstrated superior accuracy at greater z-axis depth. Overall mean TRE was 1.28±0.79 for the EM field generator having the central opening, and 1.13±0.72 for the AFG. Thus, with reference to FIG. 10, the trackers exhibited similar geometric accuracy, although the EM field generator having the central opening exhibited a somewhat deeper FOV (z-direction) than the AFG.

Figure 11:
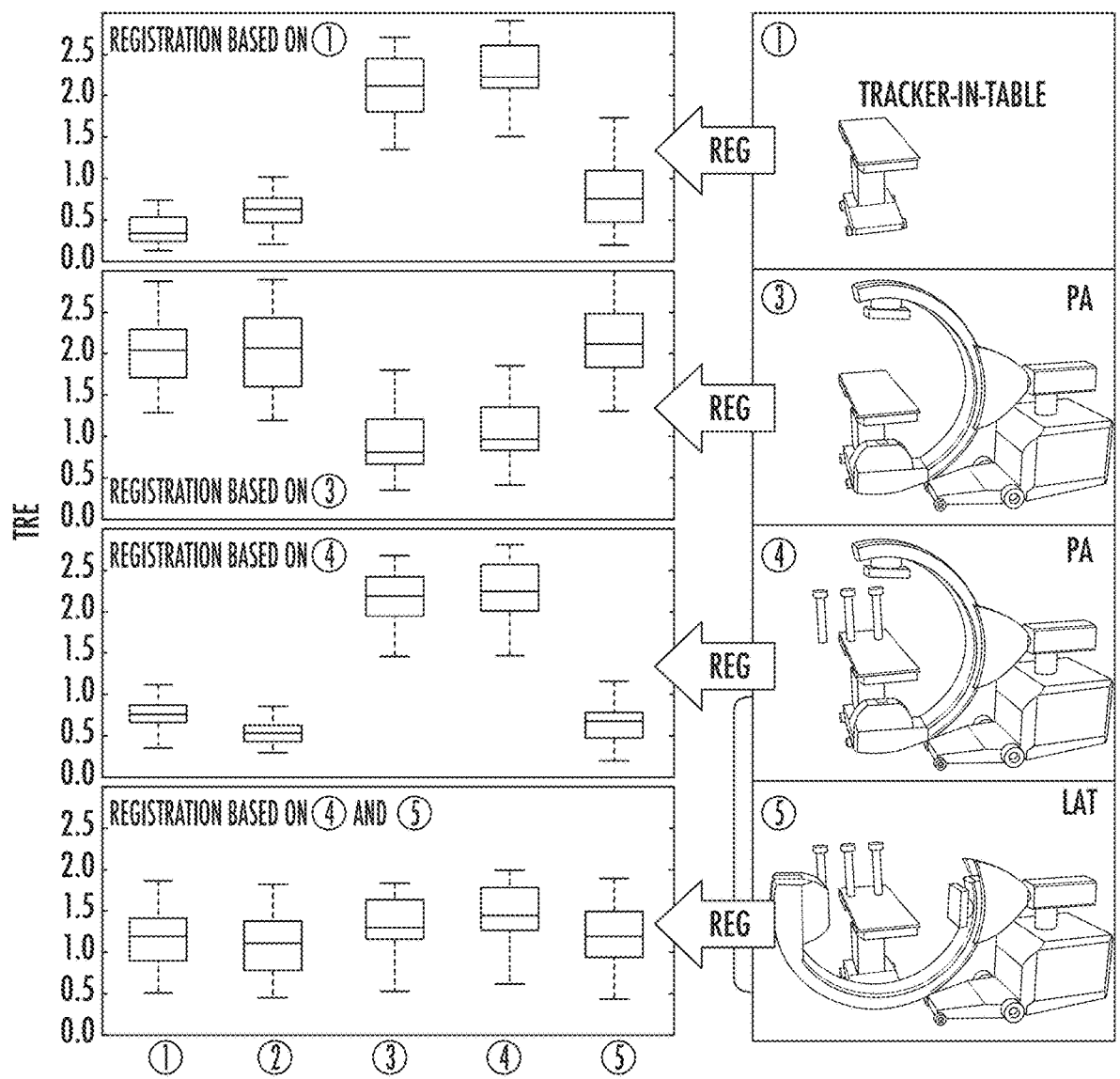
FIG. 11 depicts the TRE for various registration and measurement scenarios for an exemplary electromagnetic tracking system, as described herein.

3.2 Implementation of Tracker-in-Table in a Preclinical Setup 3.2.1 Tracking Accuracy Tracker registration was performed in each of six scenarios: (1) without either the C-arm or spine screws; (2) without the C-arm but with the three spine screws implanted; (3) with the C-arm in LAT orientation (with spine screws in place); (4) with the C-arm in PA orientation (no spine screws); (5) with the C-arm in PA orientation (with spine screws in place); and (6) a combination of setup (3) and (4)—effectively achieving an average of registrations in LAT and PA C-arm orientations. The average registration was calculated as follows: the fiducial point measurements were performed separately in configurations (3) and (4), and the two measured locations (in the tracker coordinate system, $F_{Tracker}$) of the same fiducial were averaged; subsequently, the point-based tracker-to-image registration in the CT coordinate system, $F_{CT}$, was computed using the averaged coordinates of the fiducials (FIG. 11). Results showed negligible (<0.1 mm difference) effect of the spine screws on registration accuracy (presumably due to negligible distortion of the EM field); therefore, results for the registration scenarios "with spine screws" and "with the C-arm in LAT orientation (no spine screws)" are not shown (equivalent to (1) and (4), respectively).

As depicted in FIG. 11, good geometric accuracy was achieved under the simple case in which tracker registration was performed in the absence of the C-arm (corresponding to measurement scenario (1)), where TRE was 0.39±0.43 mm. Introduction of spine screws (scenario 2) increased TRE slightly to 0.60±0.21 mm. Under the same registration scenario (1), introducing the C-arm in LAT orientation (scenario 3) increased the TRE significantly to 0.83±0.43 mm. More severe degradation in accuracy was observed with the C-arm in PA orientation, giving TRE of 2.10±0.38 mm and 2.26±0.38 mm in scenarios (4) and (5), respectively. These results show that although the performance of the EM field generator having the central opening was not degraded by a handful of spine screws in the FOV, the presence of the C-arm caused significant distortion—especially in PA orientation—and motivated alternative registration scenarios.

FIG. 11 also shows results for such a modified registration scenario, where tracker-image registration was computed with the C-arm in LAT orientation (3). The accuracy is accordingly improved in the corresponding measurement scenario (3), with TRE of 0.58±0.27 mm. The TRE in scenarios (1) and (2) was essentially the same as in the previous case. However, placement of the C-arm in the PA orientation again met with significantly degraded TRE of 2.14±0.32 mm and 2.24±0.35 mm for scenarios (4) and (5), respectively.

FIG. 11 shows analogous results for registration scenario (4) in which tracker-image registration was computed with the C-arm in PA orientation. The accuracy was accordingly improved in the corresponding measurement scenario (4) and (5)—TRE of 0.92±0.41 mm and 1.04±0.39 mm, respectively—but accuracy was degraded when the C-arm moved to LAT orientation (3) or when removed from tableside (1) or (2). The results of scenario (3), together with those of scenario (2), suggest that accurate tracking could be achieved only under conditions corresponding closely to those at the time of registration. While the TRE resulting in alternative conditions is arguably acceptable (about 2-3 mm) for some guidance applications, the results motivated further investigation of a registration scenario that could offer robust tracking at any C-arm orientation.

A reasonable compromise in registration accuracy was found in registration scenario (5), with results shown in FIG. 11. This registration scheme uses a set of corresponding registration fiducial points measured with the C-arm in both PA and LAT position. The average position for each fiducial point was determined and subsequently used in the point-based registration method. The results show reasonably accurate (<2 mm) TRE across all scenarios (although none are as accurate as the ideal case). Using the "average" registration, TRE in the range 1.0-1.5 mm was achieved with or without the C-arm and with the C-arm at any angulation.

An alternative scenario involves a plurality of tracker-to-image registrations and selection of the registration most closely corresponding to the current position and/or orientation of the tracker and associated C-arm (or other system). A further alternative involves use of a registration interpolated from a plurality of such registrations as an estimate of a tracker-to-image transformation.

FIG. 11 provides box-and-whisker plots representing: the median TRE (horizontal line), the 25th and 75th percentiles (edges of the box), and total range (extent of whiskers) excluding outliers (• symbols), with outliers defined as greater than 1.5*inter-quartile range below the first or above the third quartile. The column at right illustrates four of the five registration scenarios detailed in the text involving various C-arm orientations with and without spine screws. Registration scenario #2 was omitted, since it was found equivalent to scenario #1. The presence of the C-arm had a significant impact on tracker accuracy, and no single, simple registration scenario was found that provided low TRE for all setups. However the "average" registration scenario was found to give fairly good TRE (~1.0-1.5 mm) irrespective of the C-arm orientation, suggesting a practical method for maintaining tracker accuracy in the presence of the C-arm.

3.2.2 Effect of the WFG on CBCT Image Quality

For fluoroscopic imaging, the central opening of the exemplary electromagnetic field generator allows the x-ray beam to pass without attenuation in the PA view. In oblique or LAT views, the hollow side bars of the exemplary electromagnetic field generator are visible as longitudinal shadows in the projection but are at the same level of contrast as the edges of the OR table and were not considered a detriment to fluoroscopic image quality.

Figure 12A:
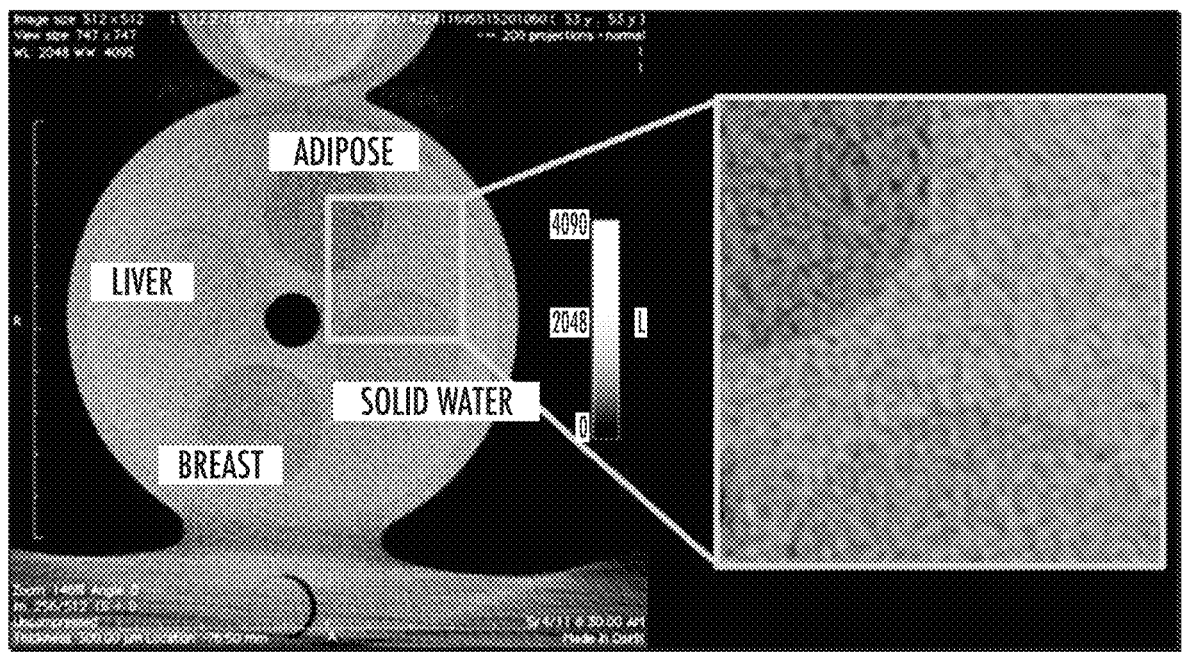
FIG. 12A-12B depicts CBCT images of a QRM Thorax acquired using an electromagnetic field generator (a) without a central opening and (b) with a central opening, as described herein.
Figure 12B:
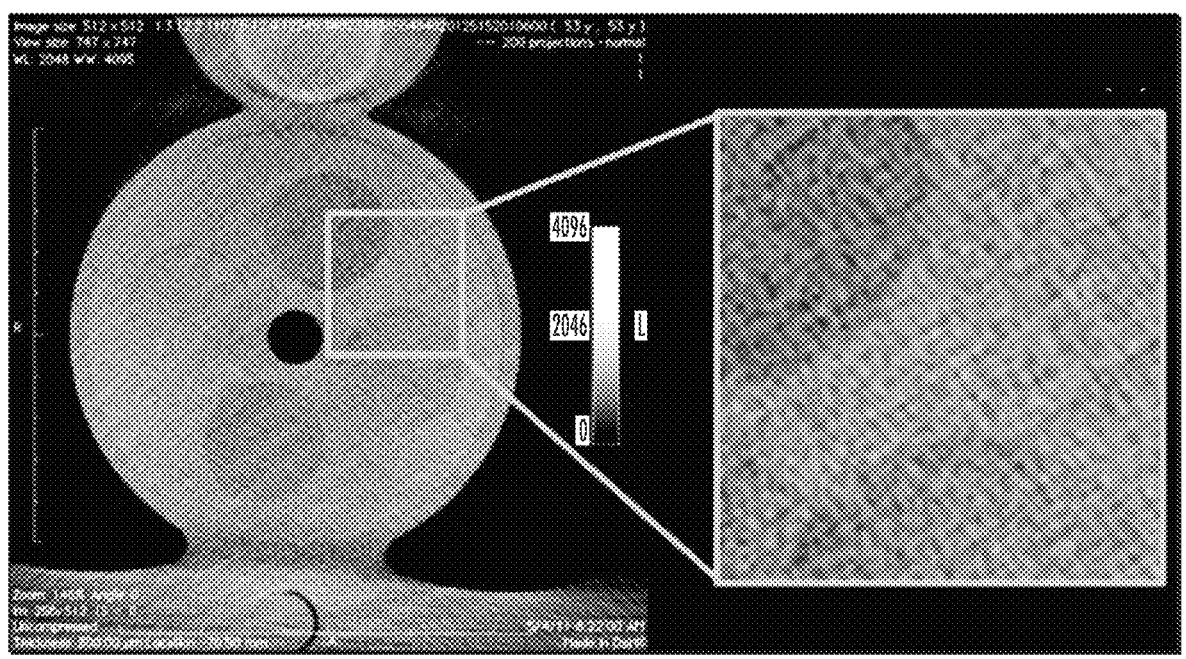
Figure 13A:
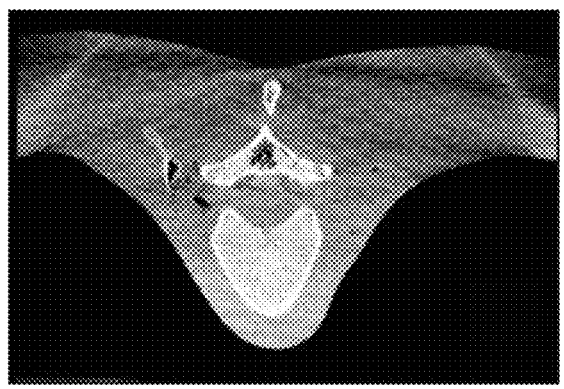
FIG. 13A-13F depicts CBCT images acquired using an electromagnetic field generator (a-c) without a central opening and (d-f) with a central opening, as described herein.
Figure 13D:
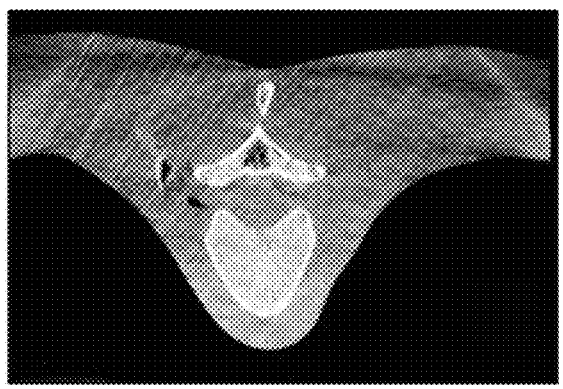
Figure 13B:
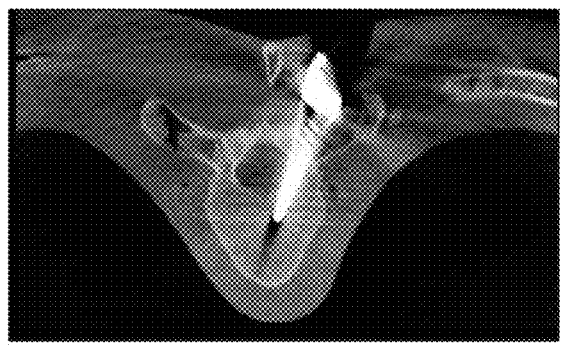
Figure 13E:
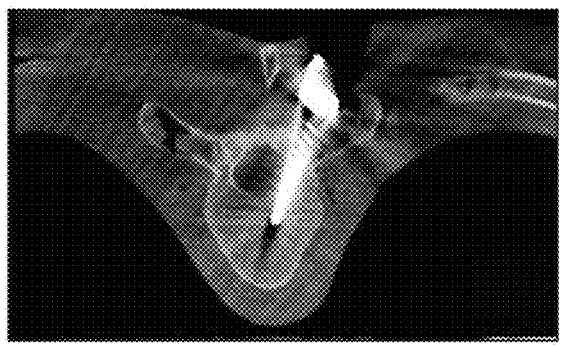
Figure 13C:
Figure 13F:

Each phantom (QRM Thorax phantom and the anthropomorphic chest phantom, including three spine screws in the T1, T5, and T7 vertebrae) was scanned on the CBCT C-arm with and without the exemplary electromagnetic field generator under the OR table. As shown in FIG. 12, the presence of the exemplary electromagnetic field generator having the central opening introduced appreciable streak artifacts comparable in magnitude to relevant soft-tissue contrasts. The artifacts impart an increase in noise in the form of streak artifacts directed approximately toward the 5 o'clock and 7 o'clock directions in FIG. 12(b), consistent with the location of the side-bars of the exemplary electromagnetic field generator outside the 3D field of view.

The effect on image quality was analyzed quantitatively in terms of CNR in the various tissue-equivalent inserts in the QRM phantom shown in FIG. 12. CBCT images were acquired under three configurations to identify the source of the streak artifacts: i.) the OR table alone; ii.) the table with acrylic support rails underneath (but without the tracker); and iii.) the table, support rails, and the exemplary electromagnetic field generator having the central opening. The acrylic support rails under the OR table were found to impart a small but measurable level of streak artifact, reducing the CNR in soft-tissue inserts by ~10%. The major source of artifacts was, however, the side-bars of the exemplary electromagnetic field generator itself. Although the side-bars are nominally hollow (with just three thin wires running in one arm connecting the EM coils), the material of the side-bars is fairly dense, and the shape of the side-bars is sub-optimal (rectangular, rather than rounded). As a result, the streak artifacts shown in FIG. 7 had an appreciable effect on soft-tissue detectability, reducing CNR by ~15% to 37% depending on the location in the FOV. Sharp edges in the projection data (e.g., the sharp corners of the sidebars) are associated with increased streaks in CBCT reconstructions due to view sampling effects and accentuation by the ramp filter in filtered backprojection. Thus, it is contemplated that re-engineering of the side bars of exemplary electromagnetic field generator using a lighter and rounded shape can improve image quality in soft-tissue imaging tasks.

The anthropomorphic chest phantom with spine screws (T1, T5, and T7) inserted was scanned without and with the Tracker-in-Table. Evaluation focused on the effect of streak artifacts in the context of high-contrast anatomy (bones) under conditions of artifacts typical of interventional imaging (i.e., streak and beam hardening in the presence of pedicle screws). As shown in FIG. 13, although the same streak artifacts arising from the Tracker-in-Table were detectable in the images, the spine screws were clearly distinguishable, and the overall degradation in the ability to perform high-contrast visualization tasks was minimal. Image subtraction was performed between images in FIGS. 13(a) and 13(d) to evaluate the relative magnitude of streak artifacts, which generally manifest as higher intensities than the surrounding structures. Results showed the streak artifact intensities to be in the range of (or slightly higher than) the contrast of simulated soft tissue. This places the magnitude of the streak artifacts in the range of soft-tissues, potentially degrading soft-tissue visibility as shown in FIG. 12, but with fairly small effect on high-contrast structure visibility in FIG. 13. CBCT images (FIGS. 13a-c) without and (FIGS. 13d-f) with the Tracker-in-Table were recorded. In (b, c, e, and f) the metallic pedicle screw (purposely placed in the anthropomorphic phantom with a slight medial breach of the spinal canal) created a significant degree of streak artifact, but the streaks associated with the exemplary electromagnetic field generator having the central opening were fairly small relative to high-contrast (bone) anatomical visualization and did not further impede the task of assessing screw placement (i.e., detection of canal breach).

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. An electromagnetic tracking system comprising:
   a patient support element having a longitudinal axis, a transverse axis, and a patient contact surface, the transverse axis of the patient support element being perpendicular to the longitudinal axis of the patient support element; and
   an electromagnetic field generator, the electromagnetic field generator being selectively moveable along at least one of the longitudinal axis and the transverse axis of the patient support element,
   wherein the patient contact surface of the patient support element is superposed relative to at least a portion of the electromagnetic field generator and wherein the patient support table is vertically spaced from the electromagnetic field generator by a selected distance.

2. The electromagnetic tracking system of claim 1, wherein the electromagnetic field generator is operatively coupled to the patient support element.

3. The electromagnetic tracking system of claim 2, wherein the patient support element comprises a patient support table.

4. The electromagnetic tracking system of claim 3, wherein the patient support table comprises a pair of spaced brackets extending parallel to the longitudinal axis of the patient support table, and wherein the pair of spaced brackets are configured to slidingly receive the electromagnetic field generator.

5. The electromagnetic tracking system of claim 4, wherein the electromagnetic field generator has an lower surface and an upper surface, and wherein the electromagnetic field generator defines a central opening through the lower surface and the upper surface.

6. The electromagnetic tracking system of claim 5, wherein the electromagnetic field generator comprises a plurality of coils spaced about the central opening of the electromagnetic field generator, wherein the spacing of the plurality of coils about the central opening is configured to permit transmission of radiation through the central opening without contacting the plurality of coils.

7. The electromagnetic tracking system of claim 5, wherein the electromagnetic field generator comprises a first coil assembly and a second coil assembly, the first coil assembly being in electrical communication with the second coil assembly, wherein the first coil assembly is oriented parallel to the second coil assembly, and wherein the first coil assembly is spaced in opposition to the second coil assembly across the central opening of the electromagnetic field generator.

8. The electromagnetic tracking system of claim 7, wherein the first and second coil assemblies of the electromagnetic field generator respectively comprise a plurality of coils that are spaced apart in a direction parallel to the longitudinal axis of the patient support table.

9. The electromagnetic tracking system of claim 7, wherein the first and second coil assemblies of the electromagnetic field generator respectively comprise a plurality of coils that are spaced apart in a direction parallel to the transverse axis of the patient support table.

10. The electromagnetic tracking system of claim 7, wherein the electromagnetic field generator comprises first and second coil housing arms and first and second side arms that cooperate to define the central opening of the electromagnetic field generator, wherein the first coil assembly is positioned within the first coil housing arm and the second coil assembly is positioned within the second coil housing arm, and wherein the first and second side arms are connected to and oriented perpendicular to the first and second coil housing arms.

11. The electromagnetic tracking system of claim 10, wherein the first and second side arms of the electromagnetic field generator are hollow.

12. The electromagnetic tracking system of claim 11, wherein the first and second side arms each have respective side edges, and wherein at least a portion of the side edges of the first and second side arms are rounded.

13. The electromagnetic tracking system of claim 4, wherein the electromagnetic field generator comprises one or more radio-translucent materials.

14. The electromagnetic tracking system of claim 13, wherein the electromagnetic field generator comprises a radio-translucent sheet having a periphery surrounding a central region, and wherein the electromagnetic field generator further comprises plurality of coils spaced about the central region within the periphery of the radio-translucent sheet, wherein the spacing of the plurality of coils about the central region is configured to permit transmission of radiation through the central region without contacting the plurality of coils.

15. The electromagnetic tracking system of claim 3, wherein the patient support table comprises a pair of spaced brackets extending parallel to the transverse axis of the patient support table, and wherein the pair of spaced brackets are configured to slidingly receive the electromagnetic field generator.

16. The electromagnetic tracking system of claim 1, wherein the electromagnetic field generator is integrally positioned within the patient support element.

17. The electromagnetic tracking system of claim 1, further comprising a radiation source.

18. The electromagnetic tracking system of claim 17, wherein the electromagnetic field generator is integrally connected to the radiation source.

19. An electromagnetic tracking method, comprising:
positioning a patient on a patient support table, the patient support table having a longitudinal axis, a transverse axis, and a patient contact surface, the transverse axis of the patient support table being perpendicular to the longitudinal axis of the patient support table;
positioning an electromagnetic field generator such that the patient contact surface of the patient support table is superposed relative to at least a portion of the electromagnetic field generator, the electromagnetic field generator operatively coupled to the patient support table, and wherein the patient support table is vertically spaced from the electromagnetic field generator by a selected distance;
selectively moving the electromagnetic field generator along at least one of the longitudinal axis and the transverse axis of the patient support table;
positioning a radiation source at a selected orientation relative to the electromagnetic field generator, the radiation source being configured to selectively transmit radiation toward the patient;
selectively activating the radiation source; and
selectively activating the electromagnetic field generator.

20. The electromagnetic tracking method of claim 19, wherein the electromagnetic field generator has a lower surface and an upper surface, wherein the electromagnetic field generator defines a central opening through the lower surface and the upper surface, and wherein the step of positioning the radiation source at a selected orientation relative to the electromagnetic field generator comprises positioning the imaging device such that radiation from the imaging device is selectively transmittable through the central opening of the electromagnetic field generator.

21. The electromagnetic tracking method of claim 19, wherein the electromagnetic field generator has a lower surface and an upper surface, wherein the electromagnetic field generator comprises first and second coil housing arms and first and second side arms that cooperate to define a central opening extending through the lower surface and the upper surface of the electromagnetic field generator, a first coil being positioned within the first coil housing arm and a second coil being positioned within the second coil housing arm, the first coil being in electrical communication with and oriented parallel to the second coil, wherein the first and second side arms are connected to and oriented perpendicular to the first and second coil housing arms, wherein the first and second side arms of the electromagnetic field generator are hollow, and wherein the step of positioning the imaging device at a selected orientation relative to the electromagnetic field generator comprises positioning the imaging device such that radiation from the radiation source is selectively transmittable through at least one of (a) the central opening of the electromagnetic field generator and (b) the first and second side arms of the electromagnetic field generator.

22. The electromagnetic tracking method of claim 19, further comprising selectively moving the electromagnetic field generator along at least one of the longitudinal axis and the transverse axis of the patient support table.

23. The electromagnetic tracking method of claim 19, wherein the step of moving the electromagnetic field generator comprises manually moving the electromagnetic field generator.

24. The electromagnetic tracking method of claim 19, wherein the step of moving the electromagnetic field generator comprises, by a computer, moving the electromagnetic field generator in an automated fashion depending upon the monitored position of a surgical tool.

25. The electromagnetic tracking method of claim 19, wherein the radiation source comprises a C-arm, the method further comprising:
   positioning the C-arm at a first position and orientation relative to the patient;
   positioning a surgical tool at a first position relative to the patient;
   using a first coordinate system associated with the patient support table, determining a first coordinate set indicative of the first position of the surgical tool;
   using a second coordinate system associated with the C-arm, determining a second coordinate set indicative of the first position of the surgical tool; and
   calculating a transformation suitable for determining a coordinate set from the first coordinate system that corresponds to a coordinate set from the second coordinate system.

26. An electromagnetic tracking method, comprising:
   positioning a patient on a patient support table, the patient support table having a longitudinal axis, a transverse axis, and a patient contact surface, the transverse axis of the patient support table being perpendicular to the longitudinal axis of the patient support table;
   positioning an electromagnetic field generator such that the patient contact surface of the patient support table is superposed relative to at least a portion of the electromagnetic field generator, the electromagnetic field generator operatively coupled to the patient support table;
   selectively moving the electromagnetic field generator along at least one of the longitudinal axis and the transverse axis of the patient support table;
   positioning a radiation source at a selected orientation relative to the electromagnetic field generator, the radiation source being configured to selectively transmit radiation toward the patient;
   selectively activating the radiation source;
   selectively activating the electromagnetic field generator; and
   wherein the electromagnetic field generator has a lower surface and an upper surface, wherein the electromagnetic field generator comprises first and second coil housing arms and first and second side arms that cooperate to define a central opening extending through the lower surface and the upper surface of the electromagnetic field generator, a first coil being positioned within the first coil housing arm and a second coil being positioned within the second coil housing arm, the first coil being in electrical communication with and oriented parallel to the second coil, wherein the first and second side arms are connected to and oriented perpendicular to the first and second coil housing arms, wherein the first and second side arms of the electromagnetic field generator are hollow, and wherein the step of positioning the imaging device at a selected orientation relative to the electromagnetic field generator comprises positioning the imaging device such that radiation from the radiation source is selectively transmittable through at least one of (a) the central opening of the electromagnetic field generator and (b) the first and second side arms of the electromagnetic field generator.

\* \* \* \* \*